United States Patent
Reichert et al.

[11] Patent Number: 5,832,165
[45] Date of Patent: Nov. 3, 1998

[54] COMPOSITE WAVEGUIDE FOR SOLID PHASE BINDING ASSAYS

[75] Inventors: W. Monty Reichert, Durham, N.C.; James N. Herron, Salt Lake City, Utah; Douglas A. Christensen, Salt Lake City, Utah; Hsu-Kun Wang, Salt Lake City, Utah

[73] Assignee: University of Utah Research Foundation, Salt Lake City, Utah

[21] Appl. No.: 705,893

[22] Filed: Aug. 28, 1996

[51] Int. Cl.$^6$ ........................................... G02B 6/10
[52] U.S. Cl. ................... 385/130; 315/12; 436/5
[58] Field of Search ................ 385/12, 129–131; 436/2, 5, 518, 317

[56] References Cited

U.S. PATENT DOCUMENTS

| | | | |
|---|---|---|---|
| Re. 33,064 | 9/1989 | Carter t al. | 436/34 |
| 4,857,273 | 8/1989 | Stewart | 385/36 |
| 4,880,752 | 11/1989 | Keck et al. | 436/807 |
| 5,081,012 | 1/1992 | Flanagan et al. | 436/172 |
| 5,156,976 | 10/1992 | Slovacek et al. | 436/807 |
| 5,166,515 | 11/1992 | Attridge | 356/246 |
| 5,344,784 | 9/1994 | Attridge | 436/807 |
| 5,512,492 | 4/1996 | Herron et al. | 385/12 |
| 5,525,466 | 6/1996 | Slovacek et al. | 385/12 |

FOREIGN PATENT DOCUMENTS

| | | |
|---|---|---|
| 0 517 516 A1 | 12/1992 | European Pat. Off. . |
| 0 519 623 A2 | 12/1992 | European Pat. Off. . |

*Primary Examiner*—John Ngo
*Attorney, Agent, or Firm*—Trask, Britt & Rossa

[57] ABSTRACT

A step-gradient composite waveguide for evanescent sensing in fluorescent binding assays comprises a thick substrate layer having one or more thin film waveguide channels deposited thereon. In one embodiment, the substrate is silicon dioxide and the thin film is silicon oxynitride. Specific binding molecules having the property of binding with specificity to an analyte are immobilized on the surface of the thin film channels. In preferred embodiments, the composite waveguide further includes light input coupling means integrally adapted to the thin film channels. Such light coupling means can be a grating etched into the substrate prior to deposition of the thin film, or a waveguide coupler affixed to the upper surface of the thin film. The waveguide coupler has a thick input waveguide of high refractive index which receives the laser light through one end and propagates it by total internal reflection. The propagated light is then coupled evanescently into the thin film waveguide across a spacer layer of precise thickness and having an index of refraction lower than either the input waveguide or the thin-film waveguide. The composite waveguide can be constructed by plasma vapor deposition of silicon oxynitride onto the silicon dioxide substrate, masking the channel waveguides with a photoresist, and using reactive ion etching to expose the substrate in the unmasked regions.

12 Claims, 25 Drawing Sheets

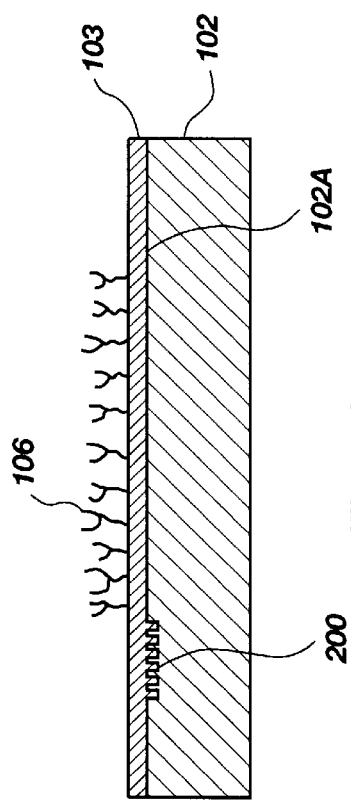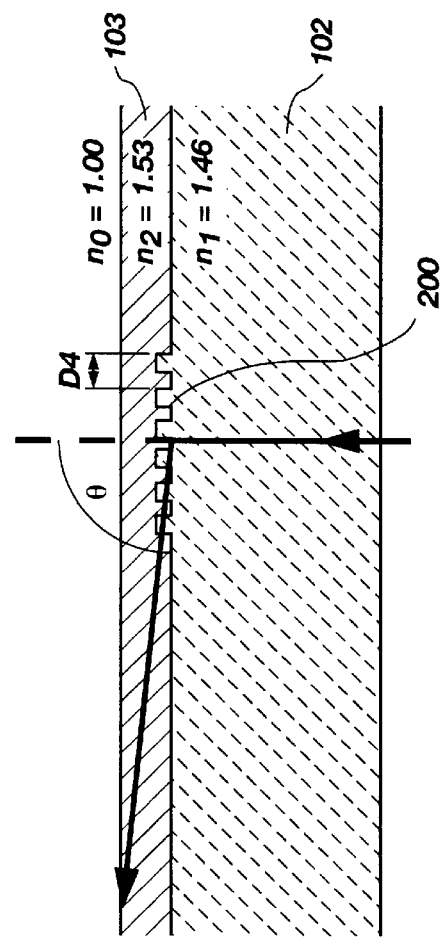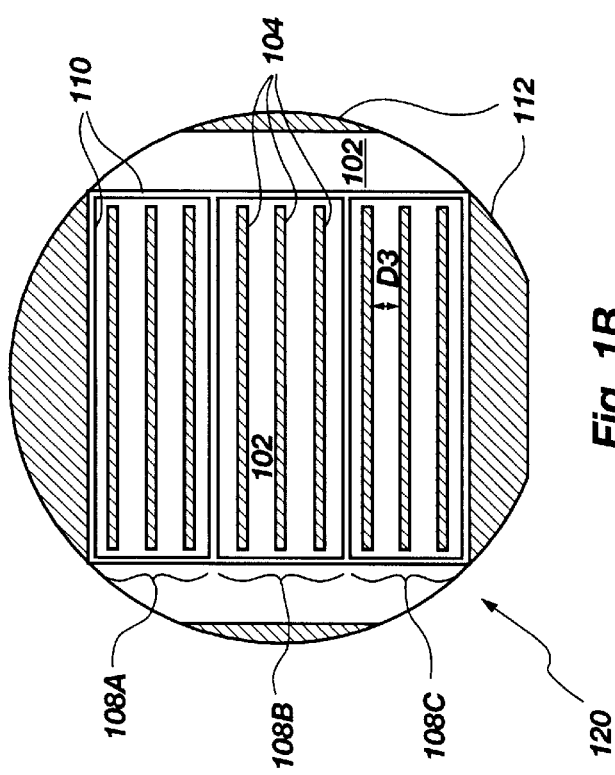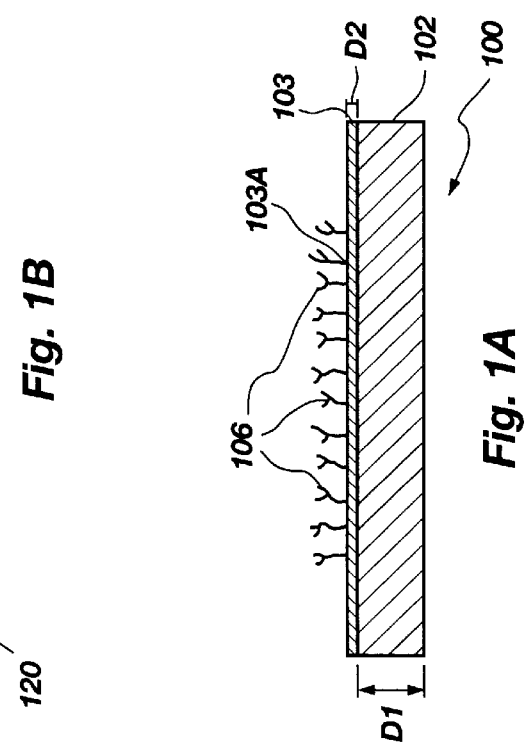

POLYSTYRENE OLIGO ASSAY

| | B | C | D | E | F | G | H |
|---|---|---|---|---|---|---|---|
| 1 | | $1 \times 10^{-12}$ M | | | | | |
| 2 | | | | | | | |
| 3 | | Raw Fluorescence Kinetic Data | | | Background Subtracted Kinetic Data | | |
| 4 | Time (min) | Ch1 | | Ch3 | $1 \times 10^{-12}$Ch1 | | $1 \times 10^{-12}$Ch3 |
| 5 | 0 | 1031980 | | 947053 | 0 | | 0 |
| 6 | 1 | 1051720 | | 964657 | 19740 | | 17604 |
| 7 | 2 | 1059810 | | 971060 | 27830 | | 24007 |
| 8 | 3 | 1064300 | | 975759 | 32320 | | 28706 |
| 9 | 4 | 1066790 | | 977556 | 34810 | | 30503 |
| 10 | 5 | 1070240 | | 979930 | 38260 | | 32877 |
| 11 | 6 | 1073240 | | 985923 | 41260 | | 38870 |
| 12 | 7 | 1077290 | | 982526 | 45310 | | 35473 |
| 13 | 8 | 1077920 | | 986607 | 45940 | | 39554 |
| 14 | 9 | 1079540 | | 984734 | 47560 | | 37681 |
| 15 | 10 | 1080120 | | 988538 | 48140 | | 41485 |
| 16 | 11 | 1083400 | | 988133 | 51420 | | 41080 |
| 17 | 12 | 1081750 | | 988906 | 49770 | | 41853 |
| 18 | 13 | 1083850 | | 990135 | 51870 | | 43082 |
| 19 | 14 | 1084520 | | 993928 | 52540 | | 46875 |
| 20 | 15 | 1086060 | | 991629 | 54080 | | 44576 |
| 21 | 16 | 1087080 | | 993243 | 55100 | | 46190 |
| 22 | 17 | 1085270 | | 994081 | 53290 | | 47028 |
| 23 | 18 | 1086270 | | 992415 | 54290 | | 45362 |
| 24 | 19 | 1087740 | | 993538 | 55760 | | 46485 |
| 25 | 20 | 1087370 | | 995980 | 55390 | | 48927 |
| 26 | 21 | 1087260 | | 994168 | 55280 | | 47115 |
| 27 | 22 | 1087940 | | 995014 | 55960 | | 47961 |
| 28 | 23 | 1089060 | | 996124 | 57080 | | 49071 |
| 29 | 24 | 1088160 | | 995082 | 56180 | | 48029 |
| 30 | 25 | 1089260 | | 997941 | 57280 | | 50888 |

*Fig. 17*

POLYSTYRENE OLIGO ASSAY

| | K | L | M | N | O | P | Q |
|---|---|---|---|---|---|---|---|
| 1 | | $1 \times 10^{-11}$ M | | | | | |
| 2 | | | | | | | |
| 3 | | Raw Fluorescence Kinetic Data | | | Background Subtracted Kinetic Data | | |
| 4 | Time (min) | Ch1 | | Ch3 | $1 \times 10^{-11}$Ch1 | | $1 \times 10^{-11}$Ch3 |
| 5 | 0 | 1112100 | | 1013190 | 0 | | 0 |
| 6 | 1 | 1152800 | | 1051900 | 40700 | | 38710 |
| 7 | 2 | 1177670 | | 1071660 | 65570 | | 58470 |
| 8 | 3 | 1195110 | | 1086710 | 83010 | | 73520 |
| 9 | 4 | 1206770 | | 1098220 | 94670 | | 85030 |
| 10 | 5 | 1218050 | | 1107530 | 105950 | | 94340 |
| 11 | 6 | 1226500 | | 1115620 | 114400 | | 102430 |
| 12 | 7 | 1235640 | | 1122820 | 123540 | | 109630 |
| 13 | 8 | 1242310 | | 1131140 | 130210 | | 117950 |
| 14 | 9 | 1250250 | | 1135680 | 138150 | | 122490 |
| 15 | 10 | 1253080 | | 1140810 | 140980 | | 127620 |
| 16 | 11 | 1262270 | | 1146620 | 150170 | | 133430 |
| 17 | 12 | 1264930 | | 1151130 | 152830 | | 137940 |
| 18 | 13 | 1271750 | | 1155150 | 159650 | | 141960 |
| 19 | 14 | 1275570 | | 1160520 | 163470 | | 147330 |
| 20 | 15 | 1279790 | | 1162120 | 167690 | | 148930 |
| 21 | 16 | 1283360 | | 1170450 | 171260 | | 157260 |
| 22 | 17 | 1289100 | | 1172750 | 177000 | | 159560 |
| 23 | 18 | 1292270 | | 1180160 | 180170 | | 166970 |
| 24 | 19 | 1292130 | | 1180470 | 180030 | | 167280 |
| 25 | 20 | 1296600 | | 1182910 | 184500 | | 169720 |
| 26 | 21 | 1300090 | | 1185730 | 187990 | | 172540 |
| 27 | 22 | 1302750 | | 1186670 | 190650 | | 173480 |
| 28 | 23 | 1304940 | | 1189090 | 192840 | | 175900 |
| 29 | 24 | 1308560 | | 1188140 | 196460 | | 174950 |
| 30 | 25 | 1309440 | | 1195230 | 197340 | | 182040 |
| 31 | 26 | 2002360 | | 1980930 | 890260 | | 967740 |
| 32 | 27 | 1314400 | | 1198680 | 202300 | | 185490 |

*Fig. 18*

POLYSTYRENE OLIGO ASSAY

|   | T | U | V | W | X | Y | Z |
|---|---|---|---|---|---|---|---|
| 1 |   | $1\times10^{-10}$ M |   |   |   |   |   |
| 2 |   |   |   |   |   |   |   |
| 3 |   | Raw Fluorescence Kinetic Data | | | Background Subtracted Kinetic Data | | |
| 4 | Time (min) | Ch1 |   | Ch3 | $1\times10^{-10}$Ch1 |   | $1\times10^{-10}$Ch3 |
| 5 | 0 | 1432650 |   | 1312580 | 0 |   | 0 |
| 6 | 1 | 1500170 |   | 1373250 | 67520 |   | 60670 |
| 7 | 2 | 1542830 |   | 1411670 | 110180 |   | 99090 |
| 8 | 3 | 1582310 |   | 1444560 | 149660 |   | 131980 |
| 9 | 4 | 1614050 |   | 1476000 | 181400 |   | 163420 |
| 10 | 5 | 1641770 |   | 1498500 | 209120 |   | 185960 |
| 11 | 6 | 1666940 |   | 1520160 | 234290 |   | 207580 |
| 12 | 7 | 1691120 |   | 1541210 | 258470 |   | 228630 |
| 13 | 8 | 1700740 |   | 1560130 | 278090 |   | 247550 |
| 14 | 9 | 1730010 |   | 1575870 | 297360 |   | 263290 |
| 15 | 10 | 1747540 |   | 1599050 | 314890 |   | 276470 |
| 16 | 11 | 1763960 |   | 1605980 | 331310 |   | 293400 |
| 17 | 12 | 1777990 |   | 1620430 | 345340 |   | 307850 |
| 18 | 13 | 1789310 |   | 1630300 | 356660 |   | 317720 |
| 19 | 14 | 1804540 |   | 1639820 | 371890 |   | 327240 |
| 20 | 15 | 1816140 |   | 1655440 | 383490 |   | 342860 |
| 21 | 16 | 1827680 |   | 1663840 | 395033 |   | 351260 |
| 22 | 17 | 1840680 |   | 1674570 | 408030 |   | 361990 |
| 23 | 18 | 1851760 |   | 1680090 | 419110 |   | 367510 |
| 24 | 19 | 1858720 |   | 1693450 | 426070 |   | 380870 |
| 25 | 20 | 1869390 |   | 1699100 | 436740 |   | 386520 |
| 26 | 21 | 1877230 |   | 1708640 | 444580 |   | 396060 |
| 27 | 22 | 1884240 |   | 1714860 | 451590 |   | 402280 |
| 28 | 23 | 1891760 |   | 1720530 | 459110 |   | 407950 |
| 29 | 24 | 1899320 |   | 1725140 | 466670 |   | 412560 |
| 30 | 25 | 1904700 |   | 1733780 | 472050 |   | 421200 |
| 31 | 26 | 1910260 |   | 1739570 | 477610 |   | 426990 |
| 32 | 27 | 1917760 |   | 1741990 | 485110 |   | 429410 |
| 33 | 28 | 1924070 |   | 1750590 | 491420 |   | 438010 |
| 34 | 29 | 1926800 |   | 1751600 | 494150 |   | 439020 |

*Fig. 19*

POLYSTYRENE OLIGO ASSAY

| | AC | AD | AE | AF | AG | AH | AI |
|---|---|---|---|---|---|---|---|
| 1 | | $1 \times 10^{-9}$ M | | | | | |
| 2 | | | | | | | |
| 3 | | Raw Fluorescence Kinetic Data | | | Background Subtracted Kinetic Data | | |
| 4 | Time (min) | Ch1 | | Ch3 | $1 \times 10^{-9}$ Ch1 | | $1 \times 10^{-9}$ Ch3 |
| 5 | 0 | 2277600 | | 2066020 | 0 | | 0 |
| 6 | 1 | 2791580 | | 2504350 | 513980 | | 438330 |
| 7 | 2 | 3116840 | | 2792860 | 839240 | | 726840 |
| 8 | 3 | 3377790 | | 3021480 | 1100190 | | 955460 |
| 9 | 4 | 3593810 | | 3217180 | 1316210 | | 1151160 |
| 10 | 5 | 3782480 | | 3389790 | 1504880 | | 1323770 |
| 11 | 6 | 3954890 | | 3544790 | 1677290 | | 1478770 |
| 12 | 7 | 4107890 | | 3684630 | 1830290 | | 1618610 |
| 13 | 8 | 4254390 | | 3819870 | 1976790 | | 1753850 |
| 14 | 9 | 4384410 | | 3940160 | 2106810 | | 1874140 |
| 15 | 10 | 4503520 | | 4046970 | 2225920 | | 1980950 |
| 16 | 11 | 4617170 | | 4155710 | 2339570 | | 2089690 |
| 17 | 12 | 4720460 | | 4250340 | 2442860 | | 2184320 |
| 18 | 13 | 4825950 | | 4345730 | 2548350 | | 2279710 |
| 19 | 14 | 4916650 | | 4431590 | 2639050 | | 2365570 |
| 20 | 15 | 5012020 | | 4517220 | 2734420 | | 2451200 |
| 21 | 16 | 5101450 | | 4600800 | 2823850 | | 2534780 |
| 22 | 17 | 5184010 | | 4676650 | 2906410 | | 2610630 |
| 23 | 18 | 5258160 | | 4747450 | 2980560 | | 2681430 |
| 24 | 19 | 5331160 | | 4812870 | 3053560 | | 2746850 |
| 25 | 20 | 5403100 | | 4876800 | 3125500 | | 2810780 |
| 26 | 21 | 5469290 | | 4940820 | 3191690 | | 2874800 |
| 27 | 22 | 5527850 | | 4999840 | 3250250 | | 2933820 |
| 28 | 23 | 5590790 | | 5054350 | 3313190 | | 2988510 |
| 29 | 24 | 5645270 | | 5109750 | 3367670 | | 3043730 |
| 30 | 25 | 5700390 | | 5159770 | 3422790 | | 3093750 |
| 31 | | 5752500 | | 5207200 | 3474900 | | 3141180 |
| 32 | | 5799990 | | 5254210 | 3522390 | | 3188190 |
| 33 | | 5849310 | | 5295550 | 3571710 | | 3229530 |
| 34 | | 5894420 | | 5337760 | 3616820 | | 3271740 |
| 35 | | 5931460 | | 5374030 | 3653860 | | 3308010 |
| 36 | | 5973550 | | 5412550 | 3695950 | | 3346530 |
| 37 | | 6010260 | | 5451210 | 3732660 | | 3385190 |
| 38 | | 6044600 | | 5482710 | 3767000 | | 3416690 |
| 39 | | 0 | | 0 | | | |
| 40 | | 6116470 | | 5550920 | 3838870 | | 3484900 |
| 41 | | 6147630 | | 5578310 | 3870030 | | 3512290 |
| 42 | | 6174870 | | 5608720 | 3897270 | | 3542700 |
| 43 | | 6204650 | | 5636190 | 3927050 | | 3570170 |
| 44 | | 6231100 | | 5654760 | 3953500 | | 3588740 |
| 45 | | 6250750 | | 5682210 | 3973150 | | 3616190 |
| 46 | | 6271150 | | 5699130 | 3993550 | | 3633110 |
| 47 | | 6293540 | | 5723860 | 4015940 | | 3657840 |
| 48 | | 6307640 | | 5731930 | 4030040 | | 3665910 |
| 49 | | 6330810 | | 5752080 | 4053210 | | 3686060 |

*Fig. 20*

POLYSTYRENE OLIGO ASSAY

|    | AL | AD       | AN | AF       | AG       | AQ | AI       |
|----|----|----------|----|----------|----------|----|----------|
| 50 |    | 21973900 |    | 23388700 | 35244420 |    | 32889720 |
| 51 |    | 22108900 |    | 20474300 | 35514420 |    | 33060920 |
| 52 |    | 22225000 |    | 20568500 | 35746620 |    | 33249320 |
| 53 |    | 22324000 |    | 20659300 | 35944620 |    | 33430920 |
| 54 |    | 22442200 |    | 20773700 | 36181020 |    | 33659720 |
| 55 |    | 22524700 |    | 20894600 | 36346020 |    | 33901520 |

*Fig. 21*

POLYSTYRENE OLIGO ASSAY

| | AL | AM | AN | AO | AP | AQ | AR |
|---|---|---|---|---|---|---|---|
| 1 | | $1 \times 10^{-8}$ M | | | | | |
| 2 | | | | | | | |
| 3 | | Raw Fluorescence Kinetic Data | | | Background Subtracted Kinetic Data | | |
| 4 | Time (min) | Ch1 | | Ch3 | $1 \times 10^{-8}$ Ch1 | | $1 \times 10^{-8}$ Ch3 |
| 5 | 0 | 8703380 | | 7887680 | 0 | | 0 |
| 6 | 1 | 12702700 | | 11737900 | 3999320 | | 3850220 |
| 7 | 2 | 15420600 | | 14403300 | 6717220 | | 6515620 |
| 8 | 3 | 17653400 | | 16383800 | 8950020 | | 8496120 |
| 9 | 4 | 19565100 | | 17999500 | 10861720 | | 10111820 |
| 10 | 5 | 21173800 | | 19524900 | 12470420 | | 11637220 |
| 11 | 6 | 22610500 | | 20827400 | 13907120 | | 12939720 |
| 12 | 7 | 23890100 | | 22128500 | 15186720 | | 14240820 |
| 13 | 8 | 25099600 | | 23241100 | 16396220 | | 15353420 |
| 14 | 9 | 26178400 | | 24236400 | 17475020 | | 16348720 |
| 15 | 10 | 27228700 | | 25135700 | 18525320 | | 17248020 |
| 16 | 11 | 28247800 | | 26050500 | 19544420 | | 18162820 |
| 17 | 12 | 29125600 | | 26871000 | 20422220 | | 18983320 |
| 18 | 13 | 29933500 | | 27640300 | 21230120 | | 19752622 |
| 19 | 14 | 30841700 | | 28312900 | 22138320 | | 20425220 |
| 20 | 15 | 31585800 | | 29031300 | 22882420 | | 21143620 |
| 21 | 16 | 32377400 | | 29684100 | 23674020 | | 21796420 |
| 22 | 17 | 33057900 | | 30278200 | 24354520 | | 22390520 |
| 23 | 18 | 33764700 | | 30843200 | 25061320 | | 22955520 |
| 24 | 19 | 34358100 | | 31395300 | 25654720 | | 23507620 |
| 25 | 20 | 34882300 | | 31916400 | 26178920 | | 24028720 |
| 26 | 21 | 35476100 | | 32442900 | 26772720 | | 24555220 |
| 27 | 22 | 36033800 | | 32959400 | 27330420 | | 25071720 |
| 28 | 23 | 36568900 | | 33453700 | 27865520 | | 25566020 |
| 29 | 24 | 37028500 | | 33900500 | 28325120 | | 26012820 |
| 30 | 25 | 37445200 | | 34258400 | 28741820 | | 26370720 |
| 31 | | 37891100 | | 34633600 | 29187720 | | 26745920 |
| 32 | | 38356200 | | 35029500 | 29652820 | | 27141820 |
| 33 | | 38764900 | | 35280900 | 30061520 | | 27393220 |
| 34 | | 39118800 | | 35568000 | 30415420 | | 27680320 |
| 35 | | 39418600 | | 35916200 | 30715220 | | 28028520 |
| 36 | | 39815000 | | 36187200 | 31111620 | | 28299520 |
| 37 | | 40140900 | | 36442000 | 31437520 | | 28554320 |
| 38 | | 0 | | 0 | | | |
| 39 | | 0 | | 0 | | | |
| 40 | | 0 | | 0 | | | |
| 41 | | 20710200 | | 19168700 | 32717020 | | 30449720 |
| 42 | | 20866700 | | 19328900 | 33030020 | | 30770120 |
| 43 | | 21014600 | | 19483400 | 33325820 | | 31099120 |
| 44 | | 21168200 | | 19624400 | 33633020 | | 31361120 |
| 45 | | 21309000 | | 19780300 | 33914620 | | 31672920 |
| 46 | | 21457900 | | 19904100 | 34212420 | | 31920520 |
| 47 | | 21621800 | | 20019800 | 34540220 | | 32151920 |
| 48 | | 21741600 | | 20140200 | 34779820 | | 32392720 |
| 49 | | 21856800 | | 20248200 | 35010220 | | 32608720 |

*Fig. 22*

POLYSTYRENE OLIGO ASSAY

|    | AL | AM       | AN | AO       | AP       | AQ | AR       |
|----|----|----------|----|----------|----------|----|----------|
| 50 |    | 21973900 |    | 23388700 | 35244420 |    | 32889720 |
| 51 |    | 22108900 |    | 20474300 | 35514420 |    | 33060920 |
| 52 |    | 22225000 |    | 20568500 | 35746620 |    | 33249320 |
| 53 |    | 22324000 |    | 20659300 | 35944620 |    | 33430920 |
| 54 |    | 22442200 |    | 20773700 | 36181020 |    | 33659720 |
| 55 |    | 22524700 |    | 20894600 | 36346020 |    | 33901520 |

*Fig. 23*

POLYSTYRENE OLIGO ASSAY

|  | AU | AV | AW | AX | AY | AZ | BA |
|---|---|---|---|---|---|---|---|
| 1 |  | $1 \times 10^{-7}$ M |  |  |  |  |  |
| 2 |  |  |  |  |  |  |  |
| 3 |  | Raw Fluorescence Kinetic Data | | | Background Subtracted Kinetic Data | | |
| 4 | Time (min) | Ch1 |  | Ch3 | $1 \times 10^{-7}$Ch1 |  | $1 \times 10^{-7}$Ch3 |
| 5 | 0 | 28245300 |  | 26212000 | 0 |  | 0 |
| 6 | 1 | 35584600 |  | 32050700 | 14678600 |  | 11677400 |
| 7 | 2 | 39026200 |  | 34787600 | 21561800 |  | 17151200 |
| 8 | 3 | 41044300 |  | 36276700 | 25598000 |  | 20129400 |
| 9 | 4 | 42114200 |  | 37171300 | 27737800 |  | 21918600 |
| 10 | 5 | 42966200 |  | 37774800 | 29501800 |  | 23125600 |
| 11 | 6 | 43538500 |  | 38208800 | 30586400 |  | 23993600 |
| 12 | 7 | 43931600 |  | 38462300 | 31372600 |  | 24500600 |
| 13 | 8 | 44268000 |  | 38663800 | 32045400 |  | 24903600 |
| 14 | 9 | 44452200 |  | 38797700 | 32413800 |  | 25171400 |
| 15 | 10 | 44584500 |  | 38940900 | 32678400 |  | 25457800 |
| 16 | 11 | 44707800 |  | 39005700 | 32925000 |  | 25587400 |
| 17 | 12 | 44741300 |  | 39075000 | 32992000 |  | 25726000 |
| 18 | 13 | 44762600 |  | 39158200 | 33034600 |  | 25892400 |
| 19 | 14 | 44825600 |  | 39210600 | 33160600 |  | 25997200 |
| 20 | 15 | 0 |  | 0 |  |  |  |
| 21 | 16 | 0 |  | 0 |  |  |  |
| 22 | 17 | 0 |  | 0 |  |  |  |
| 23 | 18 | 22483000 |  | 19739100 | 33441400 |  | 26532400 |
| 24 | 19 | 22486100 |  | 19752000 | 33453800 |  | 26584000 |
| 25 | 20 | 22481800 |  | 19759100 | 33436600 |  | 26612400 |
| 26 | 21 | 22462900 |  | 19742500 | 33361000 |  | 26546000 |
| 27 | 22 | 22437500 |  | 19722500 | 33259400 |  | 26466000 |
| 28 | 23 | 22445100 |  | 19723700 | 33289800 |  | 26470800 |
| 29 | 24 | 22415700 |  | 19714400 | 33172200 |  | 26433600 |

*Fig. 24*

POLYSTYRENE OLIGO ASSAY

| Total Increase in Fluorescence (Equilibrium) Data | | | | |
|---|---|---|---|---|
| | | | | |
| Concentration (M) | Channel 1 counts | Channel 3 counts | Total counts Ch1 | Total counts Ch3 |
| $1 \times 10^{-12}$ | 57280 | 50888 | 57280 | 50888 |
| $1 \times 10^{-11}$ | 202300 | 185490 | 259580 | 236378 |
| $1 \times 10^{-10}$ | 494150 | 439020 | 753730 | 675398 |
| $1 \times 10^{-9}$ | 4053210 | 3686060 | 4806940 | 4361458 |
| $1 \times 10^{-8}$ | 36346020 | 33901520 | 41152960 | 38262978 |
| $1 \times 10^{-7}$ | 33172200 | 26433600 | 74325160 | 64696578 |

*Fig. 25*

IO OLIGO ASSAY

| | C | D | E | F | G | H | I |
|---|---|---|---|---|---|---|---|
| 5 | | Raw Fluorescence Kinetic Data | | | | | |
| 6 | | | | | | | |
| 7 | | Concentration | | | | | |
| 8 | Time (min) | $3 \times 10^{-11}$ M | $3 \times 10^{-10}$ M | $3 \times 10^{-9}$ M | $1 \times 10^{-8}$ M | $3 \times 10^{-8}$ M | $1 \times 10^{-7}$ M |
| 9 | 0 | 13403 | 13921 | 16827 | 32542 | 77025 | 174425 |
| 10 | 1 | 13441 | 13915 | 18007 | 36606 | 84937 | 182107 |
| 11 | 2 | 13458 | 14058 | 18909 | 40339 | 89541 | 189164 |
| 12 | 3 | 13469 | 14019 | 19556 | 42439 | 93142 | 193135 |
| 13 | 4 | 13547 | 14145 | 19982 | 43697 | 95188 | 195511 |
| 14 | 5 | 13454 | 14115 | 20268 | 45324 | 98929 | 197588 |
| 15 | 6 | 13538 | 14187 | 20730 | 46146 | 100143 | 198491 |
| 16 | 7 | 13467 | 14192 | 20882 | 46895 | 101259 | 198996 |
| 17 | 8 | 13489 | 14211 | 20965 | 48048 | 103359 | 200235 |
| 18 | 9 | 13431 | 14256 | 21357 | 48227 | 105623 | 200147 |
| 19 | 10 | 13485 | 14176 | 21233 | 48766 | 105865 | 200469 |
| 20 | 15 | 13455 | 14262 | 21763 | 50251 | 110981 | 199558 |
| 21 | 20 | | 14379 | 21921 | 51306 | 113911 | 199813 |
| 22 | 30 | | 14377 | 21867 | 51825 | 114547 | 198883 |
| 23 | 40 | | | | 51559 | | 201156 |
| 24 | 50 | | | | 51908 | | |
| 25 | 60 | | | | | | |

*Fig. 27*

IO OLIGO ASSAY

| | C | J | K | L | M | N | O |
|---|---|---|---|---|---|---|---|
| 5 | | Background Subtracted Fluorescence Kinetic Data | | | | | |
| 6 | | | | | | | |
| 7 | | Concentration | | | | | |
| 8 | Time (min) | $3 \times 10^{-11}$ M | $3 \times 10^{-10}$ M | $3 \times 10^{-9}$ M | $1 \times 10^{-8}$ M | $3 \times 10^{-8}$ M | $1 \times 10^{-7}$ M |
| 9 | 0 | 0 | 0 | 0 | 0 | 0 | 0 |
| 10 | 1 | 38 | -6 | 1180 | 4064 | 7912 | 7682 |
| 11 | 2 | 55 | 137 | 2082 | 7797 | 12516 | 14739 |
| 12 | 3 | 66 | 98 | 2729 | 9897 | 16117 | 18710 |
| 13 | 4 | 144 | 224 | 3155 | 11155 | 18163 | 21086 |
| 14 | 5 | 51 | 194 | 3441 | 12782 | 21904 | 23163 |
| 15 | 6 | 135 | 266 | 3903 | 13604 | 23118 | 24066 |
| 16 | 7 | 64 | 271 | 4055 | 14353 | 24234 | 24571 |
| 17 | 8 | 86 | 290 | 4138 | 15506 | 26370 | 25810 |
| 18 | 9 | 28 | 355 | 4530 | 15685 | 28598 | 25722 |
| 19 | 10 | 82 | 255 | 4406 | 16224 | 28404 | 26044 |
| 20 | 15 | 52 | 341 | 4936 | 17709 | 33956 | 25133 |
| 21 | 20 | | 458 | 5094 | 18764 | 36886 | 25388 |
| 22 | 30 | | 456 | 5049 | 19283 | 37522 | 24458 |
| 23 | 40 | | | | 19017 | | 26731 |
| 24 | 50 | | | | 19366 | | |
| 25 | 60 | | | | | | |

*Fig. 28*

IO OLIGO ASSAY

|   | Q | R | S | T | U |
|---|---|---|---|---|---|
| 5 | | | | | |
| 6 | Total Increase in Fluorescence (Equilibrium) Data | | | | |
| 7 | | | | | |
| 8 | | Concentration | Counts | Total counts | |
| 9 | | $3 \times 10^{-11}$ | 52 | 52 | |
| 10 | | $3 \times 10^{-10}$ | 456 | 508 | |
| 11 | | 0.000000003 | 5049 | 5557 | |
| 12 | | 0.00000001 | 19366 | 24923 | |
| 13 | | 0.00000003 | 37522 | 62445 | |
| 14 | | 0.0000001 | 26731 | 89176 | |
| 15 | | | | | |
| 16 | | | | | |
| 17 | | | | | |

Fig. 29

COMPOSITE WAVEGUIDE FOR SOLID PHASE BINDING ASSAYS

License Rights. The research supporting this invention was partially funded by National Institute of Health Grant #HL32132. The United States Government may have some rights in this invention.

BACKGROUND OF THE INVENTION

Field of the Invention: The invention relates to apparatus for solid-state biochemical binding assays, and especially to optical structures utilizing evanescent sensing principles for use in such apparatus and assays.

State of the Art: Immunoassays exploiting the properties of an optical technique known as total internal reflection (abbreviated TIR) are proving to be a valuable tool for detection of analytes at concentrations of $10^{-10}$ to $10^{-13}$ molar or below, without a wash step. When a light beam traveling in a waveguide is totally internally reflected at the interface between the waveguide and an adjacent medium having a lower refractive index, a portion of the electromagnetic field of the TIR light penetrates shallowly into the adjacent medium. This phenomenon is termed an "evanescent penetration" or "evanescent light". The intensity of evanescent light drops off exponentially with distance from the waveguide surface.

Binding assays in general are based on the strong affinity of a selected "capture" molecule to specifically bind a desired analyte. The capture molecule/analyte pair can be an antibody/antigen pair or its converse, a receptor/ligand pair or its converse, etc. as known in the art. In a fluorescent binding assay, the binding of the analyte to the antibody is monitored by a tracer molecule which emits fluorescent light in response to excitation by an input light beam.

One of several possible schemes for exploiting the properties of evanescent light fields for fluorescence measurements is as follows. If an antibody is immobilized on an optical structure in which a light beam is being propagated by TIR, the resulting evanescent light can be used to selectively excite tracer molecules that are bound (whether directly or indirectly) to the immobilized antibody. Tracer molecules free in solution beyond the evanescent penetration depth are not excited, and therefore do not emit fluorescence. For silica-based optical materials or optical plastics such as polystyrene, with the adjacent medium being an aqueous solution, the evanescent penetration depth is generally about 1000 to 2000 Å (angstroms). The amount of fluorescence is thus a measure of the amount of tracer bound to the immobilized capture molecules. The amount of bound tracer in turn depends on the amount of analyte present, in a manner determined by the specifics of the immunoassay procedure.

U.S. Pat. Nos. RE 33,064 to Carter, 5,081,012 to Flanagan et al, 4,880,752 to Keck, 5,166,515 to Attridge, and 5,156,976 to Slovacek and Love, and EP publications Nos. O 517 516 and 0 519 623, both by Slovacek et al, all disclose apparatus for immunoassays utilizing evanescent sensing principles.

Desirably, an immunosensor should be capable of accurately and repeatably detecting analyte molecules at concentrations of $10^{-13}$M (molar) to $10^{-15}$M and preferably below. At present, such sensitivity is not believed to be available in a commercially practical and affordable immunosensor. Also desirably, an immunosensor should provide multiple "channels", that is, the capacity for measuring multiple analytes and multiple measurements of the same analyte, on the same waveguide substrate. Such an immunosensor would allow both self-calibration with known standards, and screening for a panel of different analytes selected for a particular differential diagnostic procedure.

One approach to improving the sensitivity (lowering the detection limits) of fluorescent immunosensors, proposed by Ives et al. (Ives, J. T.; Reichert, W. M.; Lin, J. N.; Hlady, V.; Reinecke, D.; Suci, P. A.; Van Wagenen, R. A.; Newby, K.; Herron, J.; Dryden, P. and Andrade, J. D. "Total Internal Reflection Fluorescence Surface Sensors" in A. N. Chester, S. Martellucci and A. M. Verga Scheggi Eds. *Optical Fiber Sensors,* NATO ASI Series E, Vol 132, 391–397, 1987), is to use waveguides which are very thin, perhaps about 1 μm in thickness. Such thin waveguides may provide higher evanescent intensity and a reflection density of 500–1000 reflections/cm or more. However, the potential lowering of the detection limit by use of thin-film waveguides is achievable only if the waveguide material is nonfluorescent and low-loss. Most present evanescent immunosensing technology ("thick" waveguides) utilizes silica glass ($SiO_2$), which is intrinsically nonfluorescent. Only the purest grades of silica, for example UV grade quartz which is rather expensive, lack the additives and impurities that fluoresce (Dierker, et al., 1987).

Further, one cannot simply fabricate silica-on-silica waveguides by depositing $SiO_2$ onto a quartz substrate because there would be no refractive index difference. Instead one must either (1) fabricate a glass waveguide of higher refractive index than the underlying silica substrate, or (2) deposit a silica waveguide onto a transparent substrate of a lower refractive index. Therefore, other materials must be employed.

Thin film waveguides have been described by Sloper et al. ("A planar indium phosphate monomode waveguide evanescent field immunosensor" *Sensors and Actuators* B1:589–591, 1990) and Zhou et al. ("An evanescent fluorescence biosensor using ion-exchanged buried waveguides and the enhancement of peak fluorescence", *Biosensors and Bioelectronics* 6:595–607, 1991. However, neither of these devices was capable of achieving detection of analyte concentrations significantly below $10^{-10}$ molar. The waveguide structure of Sloper was of the gradient-index type, formed by diffusion of a dopant into the silica base, which results in a drop-off of dopant concentration with distance from the interface. The waveguide of Zhou had only a single "channel" (measurement region).

Therefore, a need exists for an optical structure useful in an evanescent sensing immunoassay, which provides increased levels of propagated TIR light and increased evanescent field intensity, as well as multiple measurement regions. Such an optical structure should desirably be capable of detecting of analyte concentrations of $10^{-13}$M and preferably below $10^{-15}$M. A need also remains for an immunosensor including such an optical structure, which is sufficiently inexpensive and practical to be produced as a commercial device, and which provides accurate and repeatable results in the hands of non-skilled persons. Still further, a need also remains for a biosensor capable of detecting ions, as opposed to just hormones or other biological molecules.

SUMMARY

The invention comprises a step gradient waveguide, also described as a composite waveguide, useful for performing evanescent sensing assays. The waveguide includes a thick substrate formed of a first optical material of refractive index $n_1$ and having a first surface, and a thin film formed of a second optical material having a refractive index $n_2$ which is greater than $n_1$, the thin film being disposed adjacent and in operative contact with the substrate. The optical substrate has a thickness which may be from about 0.3 μm up to 10 mm or more, depending on the material used, while the thin film has a thickness which is generally between about 0.3 μm and about 5 μm. Highly preferably, the waveguide thickness is selected to provide for internal propagation in from one to four modes only.

The invention further encompasses a kit comprising the composite waveguide, and at least one specific binding molecule immobilized to said thin film and constructed to bind with specificity an analyte. The kit may be further constructed for use in either a competition assay or a sandwich-type assay. The tracer molecule is further constructed to be excited by evanescent light penetrating from the thin film into an adjacent aqueous environment, and to respond thereto by emitting a photodetectable tracer signal.

In a preferred embodiment, the composite waveguide comprises the substrate with a plurality of thin strips of the thin film disposed in parallel array thereon, and the kit further includes a second solution containing a known concentration of analyte in a buffer.

In preferred embodiments of the composite waveguide, coupling means are integrally adapted and in operative contact with the thin film for coupling input light thereinto. One embodiment of coupling means is a grating etched into the substrate on the surface adjacent the thin film. Alternatively, instead of a physical grating a grating-type coupler may be composed of an array of segments of a different refractive index $n_5$ disposed in the substrate in a regular spacing analogous to that of the ridges in a grating. In another alternate embodiment, a relatively thick waveguide coupler is disposed on the planar surface of the thin film waveguide opposite the substrate, near one end of the composite waveguide. The waveguide coupler is dimensioned and constructed of appropriate optical material so as to evanescently couple light propagated by TIR in a thick input waveguide across a thin spacing layer into the thin film waveguide.

In a highly preferred embodiment, the composite waveguide is constructed by vapor deposition of the thin film on the substrate, masking of the thin strips with a resist compound, and etching the thin film to expose the substrate in the unmasked areas. The resist compound is then removed to allow immobilization of the binding molecules to the thin strips.

The invention further embraces apparatus for performing specific binding assays, the apparatus comprising a composite waveguide together with an optical unit having a light source positioned to direct light into the waveguide for propagation by total internal reflectance therein, and detection means oriented to detect light from a region proximal to the optical structure.

The (IOW) of the invention is capable of detecting analyte concentrations in the femtomolar ($10^{-18}$M) range. Such sensitivity is well beyond that achieved by other thin-film evanescent sensors, and also beyond the sensitivity expected solely on the basis of the increased reflection density intensity in the thin-film waveguide.

BRIEF DESCRIPTION OF THE DRAWINGS

In the drawings, which depict the best mode presently known for carrying out the invention:

FIG. 1A is a side cross-sectional view of the composite waveguide of the invention;

FIG. 1B is a top view of a composite waveguide module having a cross-sectional composition according to FIG. 1A;

FIG. 2A is a side view of a composite waveguide having an integral etched grating coupler;

FIG. 2B is a schematic illustration of the embodiment of FIG. 2A showing diffraction of a normal incident light beam into a guided mode of the thin film waveguide;

FIG. 17 is a compilation of data for Example 5, wherein the concentration was $1 \times 10^{-12}$M;

FIG. 18 is a compilation of data for Example 5, wherein the concentration was $1 \times 10^{-11}$M;

FIG. 19 is a compilation of data for Example 5, wherein the concentration was $1 \times 10^{-10}$M;

FIG. 20 is a compilation of data for Example 5, wherein the concentration was $1 \times 10^{-9}$M;

FIG. 21 is a continuation of the data of FIG. 20;

FIG. 22 is a compilation of data for Example 5, wherein the concentration was $1 \times 10^{-8}$M;

FIG. 23 is a continuation of the data of FIG. 22;

FIG. 24 is a compilation of data for Example 5, wherein the concentration was $1 \times 10^{-7}$M;

FIG. 25 is a chart displaying the total increase in fluorescence (Equilibrium) data for the Polystyrene oligonucleotide assay;

FIG. 27 is a compilation of the experimental results obtained from Example 6 showing the raw fluorescence kinetic data for various oligonucleotide concentrations;

FIG. 28 is a compilation of the experimental results obtained from Example 6 showing the background subtracted fluorescence kinetic data; and FIG. 29 is a compilation of data from Example 6 showing the total increase in Fluorescence (Equilibrium).

DETAILED DESCRIPTION OF THE ILLUSTRATED EMBODIMENTS

Figure 3A:
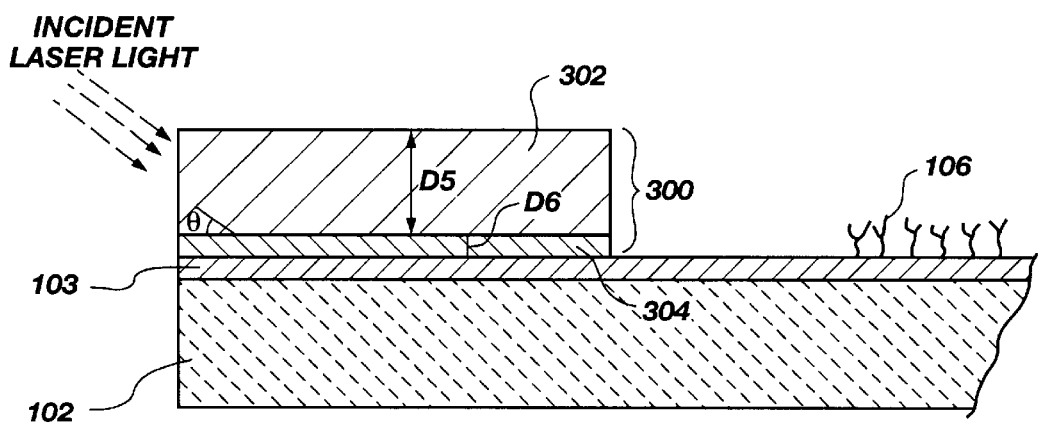
FIG. 3A is a side cross-sectional view of an alternate embodiment of a composite waveguide, having an integral waveguide coupler.

A composite waveguide indicated at 100 has a substrate 102 formed of a first optical material of refractive index $n_1$ (FIG. 1A), and a thin-film waveguide layer 103 of a second optical material of refractive index $n_2$, with $n_2$ being greater than $n_1$. The waveguide layer 103 has a plurality of binding molecules 106, each constructed to specifically bind an analyte, immobilized on the upper surface 103A. The substrate 102 has a thickness D1 which may be from about 0.3 $\mu$m up to 10 millimeters (mm) or more, while the thin-waveguide 103 has a thickness D2 of between about 0.3 microns ($\mu$m) and 5 $\mu$m. If the substrate 102 is relatively thick, perhaps 0.5 mm or more, as shown in FIG. 1A, it may also serve as a mechanical support in addition to having the optical properties necessary for supporting effective waveguiding of light in the thin film waveguide layer 103. However, in some embodiments it is preferred, generally for easier manufacture, that the substrate 102 be comparatively thin. In such cases an additional support layer (not shown) may be added below the optical substrate 102 (not shown).

In a presently preferred embodiment, the substrate 102 is silicon dioxide, either in the form of an $SiO_2$ thin film laid down by vapor deposition or other techniques as known in the art, or in the form of quartz (here defined as including both natural quartz, and fused silica or other manmade quartz), with a waveguide layer formed of silicon oxynitride ($Si_zO_xN_y$, or, generally, "SiON"). The term "deposited $SiO_2$" is used hereinafter to distinguish the deposited $SiO_2$ from quartz/fused silica, etc. Silicon dioxide has a refractive index of n=1.47, and, if sufficiently pure, exhibits very low fluorescence. Silicon oxynitride is mechanically durable, transparent in the visible wavelength range, substantially non-fluorescent, and has a refractive index generally above 1.5 and reaching as high as 2.0 depending on the stoichiometric ratios of O to N. In a further presently preferred embodiment, the SiON is $Si_2O_3N$.

In another embodiment, the substrate 102 is formed of SiON having a refractive index $n_1$ and the waveguide film 103 is formed of SiON having a refractive index $n_2>n_1$. The refractive index of the SiON compositions is controlled by the proportion of nitrogen. That is, the SiON of the substrate will have a lower proportion of nitrogen than the SiON of the waveguide film.

In still another embodiment, the substrate 102 is formed of $MgF_2$ (magnesium fluoride), refractive index n=1.38, and the waveguide layer 103 is a pure silicon dioxide thin film. Because the MgF substrate is formed by vapor deposition techniques or the like which are tedious and comparatively expensive, in this embodiment the substrate 102 need be only sufficiently thick to ensure efficient propagation of at least one guided mode. At present, the SiON waveguide layer 103 is preferred, as it provides better adherence to the substrate in aqueous solutions than the $MgF_2$ waveguide. However, the $MgF_2$ waveguide/$SiO_2$ composite waveguide may be entirely suitable for use with non-aqueous solvents.

In a presently preferred embodiment of a structure including a thin film SiON waveguide, the substrate 102 is a layer of $SiO_2$ deposited on a silicon wafer support. This is preferred because the surface of the substrate 102 is much more uniform and smooth, which in turn produces a much smoother planar surfaces in the deposited SiON film. The increased smoothness of the waveguide surfaces reduces the propagation losses by at least two-fold in comparison with a thin film waveguide deposited on a quartz or fused silica substrate.

In FIG. 1B, the waveguide layer is shown as a plurality of strips 104 which does not extend the full length of the substrate 102. This is an optional configuration of the waveguide layer designed to provide multiple waveguide "channels" for different sample solutions and/or for having different immobilized capture molecules. Further optionally, the composite waveguide 120 may be configured as a plurality of rectangular wells 108A, 108B, 108C, each containing three strips 104. The strips 104 are separated from one another by a distance D3 of at least about 5 mm. The wells 108A,B,C are separated by walls 110 extending upward from the substrate 102. The device of FIG. 1B may be formed by vapor deposition of the SiON over the entire surface of the substrate 102, masking the regions corresponding to the thin strips 104 with a resist compound, etching the exposed SiON to remove it from the substrate 102, and removing the resist compound. In FIG. 1B, shaded regions 112 represent areas of the waveguide which were not exposed to etchant. The binding molecules 106 are then immobilized to the thin strips 104. This can be accomplished by means known in the art of binding assays. Alternatively, the wells 108A, 108B, 108C may be configured for flow-cell type operation, as separate flow-through compartments for background, calibration (known analyte concentration), and test sample (unknown) solutions.

High quality composite waveguides made of the material combinations described above can be formed using plasma enhanced chemical vapor deposition (PECVD) to deposit a thin film over an entire surface of the substrate, and then lithographically etching away the thin film except in the desired strips. In the case of SiON, the PECVD is performed with a mixture of nitrogen, nitrous oxide, ammonia and silane gases, and the stoichiometry of $Si_zO_xN_y$ is varied by changing the respective partial pressures of the above components.

For the lithographic steps, it is presently preferred to use a reactive-ion etch (RIE) process with commercially available photoresist compounds. The areas of the film which are to become the strips or channels are coated with the resist, and the surrounding areas are etched down to the substrate. In the present embodiment, the DUV negative-tone photoresist XP89131 available from Shipley Co. is preferred, and the etchant is a plasma of $O_2$ and $CHCl_3$ gases. Positive tone resists such as XP2198 (Shipley Co.), APEX-E from IBM, and CAMP6 from OCG are also suitable. (All of these compositions are proprietary). All of these resist compounds are of the chemical amplification type, comprised substantially of phenolic polymers. While older photo-resists such as PMMA (polymethylmethacrylate) could be used, the chemically amplified DUV resists are considered to produce superior results for the present purposes.

Almost any other etching technique could be readily applied for etching the channels into the waveguide film, including plasma etch, ion milling, or a wet etch. However, where it is desired to use a substrate-etched grating to increase the coupling efficiency (see FIG. 2A and related description), the RIE process is preferred. This is because the etching process is critical to production of a highly anisotropic grating. RIE etching is believed to provide the best results for the grating, and wet etching would be unsuitable. For waveguides having an etched grating coupler, then, it is convenient to use the RIE process to etch the channels as well.

It is also within contemplation that the thin-film waveguide channels could be produced by a wet lift-off process. In this process, the substrate of the waveguide would be masked to leave the channel regions bare, and the SiON thin film would then be deposited over the whole surface including the masking agent. After deposition of the film, the entire surface would be immersed in a solvent selected to "lift-off" or remove the mask, together with the waveguide film deposited on the mask, while leaving the film deposited on the bare quartz.

All steps of the waveguide fabrication should be performed in an extremely clean environment, preferably a clean-room meeting the standards of at least class 10.

EXAMPLE 1

SiON Composite Waveguide Fabrication

Waveguides comprising a 1 µm thick film of $Si_2O_3N$ on $SiO_2$ have been produced as follows. A heated sample holder containing a 10.16 centimeter (4 inch) quartz wafer was placed in a plasma-enhanced chemical vapor deposition (PECVD) reactor. Process gasses flowed from the perimeter of the PECVD vessel, over the sample, and were then pumped out of the vessel through a central port. During deposition, the PECVD reactor was maintained at 300° C. and 1.25 Torr, with 50 W of power to a 13.56 MHz generator. The gas mixture consisted essentially of 27 standard cm³ per minute (sccm) silane ($SiH_4$), 500 sccm nitrogen, 200 sccm ammonia, and 1300 sccm nitrous oxide. The respective inlet partial pressures were approximately 17 mTorr, 308 mTorr, 123 mTorr, and 802 mTorr. Under these conditions, the deposition rate was about 590 Å/minute and a 1 µm film was produced in about 15 minutes. These silicon oxynitride films had an approximate elemental ratio of Si:O:N=2:3:1, and a refractive index of about n=1.53 to 1.54.

Next, the $Si_2O_3N$ films were coated with photoresist, masked, and developed to expose all but nine parallel 1 mm×65 mm strips of the SiON film separated by 5 mm. The unmasked SiON was etched down to the quartz wafer. The photoresist was stripped, and the etched wafer was cleaved to produce three 23 mm×69 mm rectangular pieces, where each piece contained three parallel 1 µm thick channel waveguides. Only the two outside channels were used in the assays described here.

There are several properties of composite waveguides which can be correlated to their relative suitability for evanescent-sensing biochemical binding assays. These include the ability to withstand the solvent used in the assay, which is generally but not always water; the amount of propagated light lost per unit distance traveled in the waveguide ("propagation loss", expressed as dB per cm); the intrinsic level of fluorescence of the waveguide upon irradiation with light of the excitation wavelength to be used, as measured within the bandwidth of the tracer fluorescence emission; reflections/cm at the waveguide-superstrate interface ($N_r$); and adequate depth of evanescent penetration ($d_p$).

EXAMPLE 2

Characterization of SiON Waveguide

Scanning electron microscopy was used to examine the shape and thickness of etched channel waveguides. A nominal channel should have optically smooth, rectangular edges and a uniform thickness. For optical characterization of channel waveguides, the beam of the 632.8 nm line from a HeNe laser was coupled into the waveguide using a prism coupler. In a typical experiment, values were determined for waveguide thickness ($t_{wg}$), refractive index ($n_{wg}$), internal reflection angle ($q_{wg}$), reflections/cm at the waveguide-superstrate interface ($N_r$), depth of penetration ($d_p$), and propagation loss (dB/cm). The data of Table 1 summarize the properties measured for a typical SiON waveguide constructed by the procedure outlined

TABLE I

Optical characterization of SiON waveguides

| waveguide parameter | air superstrate | water superstrate |
|---|---|---|
| $t_{wg}$ (µm) | 1.31 ± 0.11 | N.A. |
| $n_{wg}$ | 1.53 ± 0.0 | N.A. |
| propagation loss (dB/cm) | 0.76 ± 0.09 | N.D. |
| $q_{wg}$ (degrees) | 82.67 ± 0.47 | 82.85 ± 0.42 |
| $d_p$ (nm) | 44.10 ± 0.06 | 68.79 ± 0.29 |
| $N_r$ (reflections/cm) | 492.10 ± 71 | 479 ± 0.29 |

Each parameter was measured for three different channel waveguides with air as the superstrate. The mean and standard error of these measurements is reported. In addition, the last three parameters ($q_{wg}$, $d_p$, N) were determined when water was substituted for air as the superstrate.
N.D. — not determined.

in Example 1. Also, these waveguides possess a high degree of physical definition and the desirable features of low propagation loss and minimal intrinsic waveguide fluorescence.

EXAMPLE 3

Fabrication of $MgF_2/SiO_2$ Composite Waveguide

The $SiO_2/MgF_2$ laminates were deposited in situ by electron beam evaporation, using a multipocket electron beam gun in a Balzers BAK760 high-vacuum coater. The deposition chamber was evacuated to 2 µTorr, and the silica chips used as mechanical supports on which the laminates were deposited were heated to 200° C. The chamber pressure rose to 3.8 µTorr as a result of heating of the silica chips prior to deposition. The source materials, 99.9% pure $MgF_2$ and 99.999% pure $SiO_2$, were placed in molybdenum- and graphite-lined hearths, respectively, in the rotatable source carousel. Both source materials were brought to the deposition temperature with the shutter closed. First the $MgF_2$ was evaporated with a slowly sweeping 10-kV (kilovolt) electron beam (≈12 mm² elliptical spot size) followed by similar evaporation of the $SiO_2$. The deposition rates of $MgF_2$ and $SiO_2$ were controlled at 20 Å/s and 10 Å/s (angstroms per second), respectively, by means of an oscillating crystal monitor. A 0.36 µm film of $MgF_2$ was deposited in 3 minutes, and a 1.0 µm film of $SiO_2$ was deposited in 16 minutes.

Following construction of the physical portion of the waveguide, a plurality of specific binding molecules, that is, molecules having the property of specifically binding a chosen analyte, are immobilized on the surface of the thin film waveguide channel(s). Such specific binding molecules may be antibodies, receptor molecules, and the like, or fragments thereof that are operative to specifically bind the corresponding analyte. Converse pairs, e.g. such as an antigen for detecting certain antibodies with the analyte being the antibody, are also suitable. Other types of binding molecule/analyte pairs will be apparent to those of ordinary skill, as will means for immobilizing the binding molecule. Presently preferred means for immobilizing the binding molecule are discussed subsequently herein.

Figure 4A:
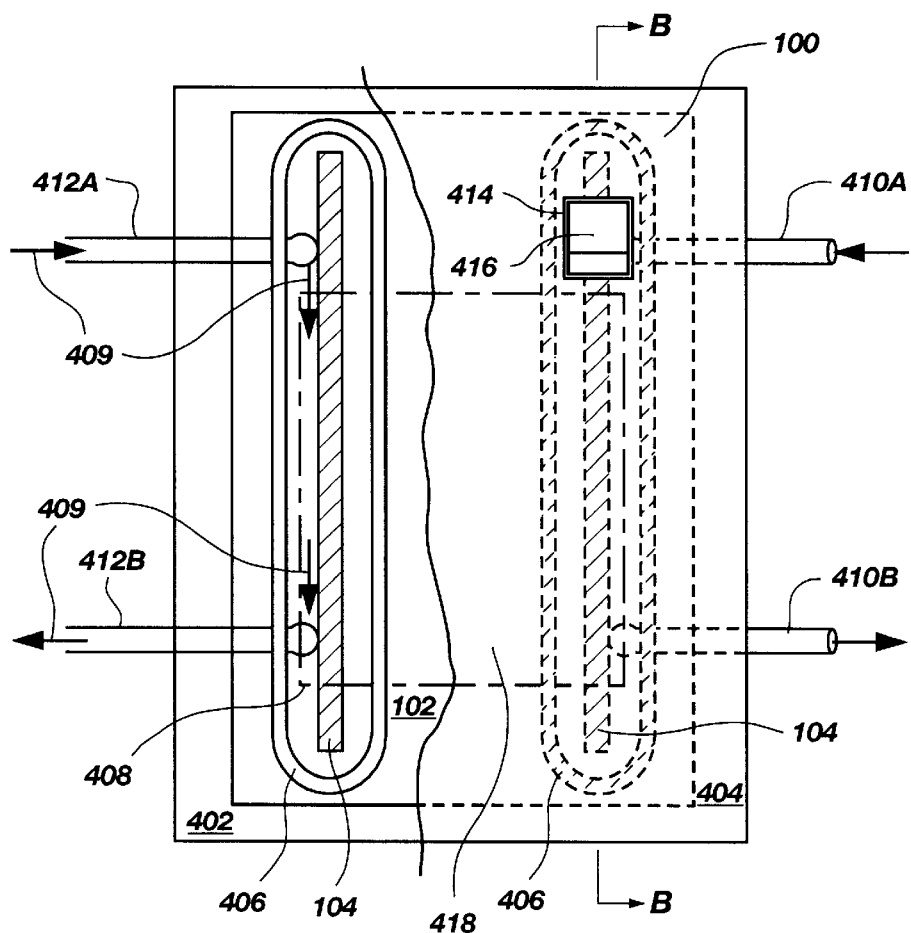
FIG. 4A is a schematic diagram of a top view with partial cutaway of a flow cell incorporating a multichannel composite waveguide.
Figure 4B:
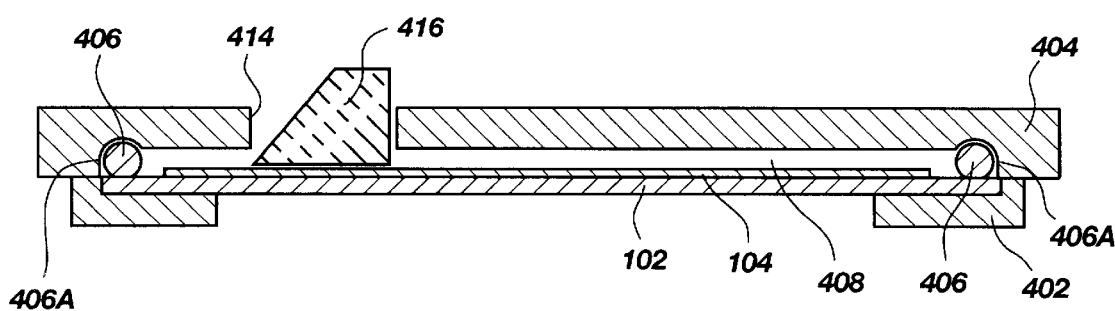
FIG. 4B is a side cross-section taken along line B—B of FIG. 4A.

A flow cell incorporating a two channel waveguide fabricated and characterized as in Examples 1 and 2 is shown in FIGS. 4A and 4B. A composite waveguide 100 is held between a bottom plate 402 and a top plate 404 spaced by a pair of black silicone rubber o-ring gaskets 406 (FIG. 4B). Each gasket is seated in a corresponding groove 406A milled in the top plate, and forms a longitudinal flow channel 408. The flow channels have respective inlet ports 410A, 412A and outlet ports 410B, 412B. Arrows 409 indicate the direction of flow of liquid through the channel 408. Each flow channel also has a hole 414 for placing a coupling prism 416. The interior of the bottom plate has a window 418 milled therein to support the waveguide and provide a clear view of the waveguide bottom through the silica chip support layer. The aluminum parts of the entire flow cell are desirably flat black, to absorb stray light. Coupling prisms (4 mm wide by 10 mm high truncated 45-45-90 LaSF prisms, $n_p$=1.83, obtained from Karl Lambrecht Co.) were fixed in place inside the windows 414 with GTE 118 RTV silicone rubber cement. A series of finger screws (not shown) were used to clamp the top and bottom plates 404, 402 to the substrate 102, and to maintain coupling pressure on the prisms 416. Polyethylene screw-in tubing connectors, TEFLON® microtubing, and disposable syringes served as the sample delivery system (not shown). The sample volume of each channel 408 was 300 µL.

Prism coupling the waveguide with aqueous superstrate comprises placing the waveguide on the bottom plate of the flow cell, wetting the waveguide surface opposite the substrate with buffer solution to be used in measurements, and then placing the top plate with the attached prisms over the wetted waveguide. An advantage of the raised-channel waveguide structure is that effective prism coupling is easily accomplished by placing mild pressure on the coupling prisms.

Evanescent binding assays in two model systems were performed with the flow cell of FIGS. 4A, 4B, using a dual-channel assay format similar to that described by Herron et al. in "Fluorescent immunosensors using planar waveguides", *SPIE Vol.* 1885 (*Advances in Fluorescence Sensing Technology*), pp. 28–39, 1993, as well as in the copending U.S. patent application Ser. Nos. 08/064,608 and 08/263,522.

EXAMPLE 4

Model Assays Using Thin-film Waveguide Flow Cell

In the first or direct-binding model system, the binding of a biotinylated antibody labelled with a fluorescent tracer to avidin immobilized on the waveguide surface was measured. The particular antibody used was an anti-fluorescein antibody designated 9-40, produced by standard hybridoma methodology. The 9-40 antibody was labelled with the dye Cy-5 ($\lambda_{abs,max}$=650 nm, $\lambda_{cm,max}$=667 nm, $e_{max}$=2×10$^5$ M$^{-1}$ cm$^{-1}$) according to the manufacturer's procedure (Biological Detection Systems). The labeling efficiency was approximately four dyes per protein molecule. An untreated hydrophilic SiON IOW surface was treated for 8 hr with a 0.2 mg/mL solution of avidin (obtained from Sigma) dissolved in phosphate buffered saline (PBS, pH 7.4), to physically adsorb the avidin to the waveguide surface.

A portion of the Cy-5 labeled 9-40 was biotinylated using N-hydroxysuccinimidobiotin (Sigma). Specifically, a 20-fold molar excess of this reagent was added to a 1 mg/mL solution of 9-40 in 0.1M sodium carbonate/sodium bicarbonate buffer, pH 9 (CBB). This mixture was allowed to react for 2 hr at room temperature, and the product (biotinylated, CY-5-conjugated 9-40) was purified by gel permeation chromatography using a PD-10 column (Pharmacia) equilibrated in PBS.

The second type of assay was an indirect, sandwich type assay in which the binding of free fluorescein-conjugated BSA to immobilized anti-fluorescein antibody (antibody 9-40) was measured using an anti-BSA antibody conjugated with Cy-5 as a tracer. The IOW surfaces with immobilized 9-40 antibody was prepared as follows. Prior to immobilization, 9-40 was acid pre-treated in citrate buffer (pH 3) for 1 hr and reconstituted in PBS at a concentration of 2.3×10$^{-7}$M (0.03 mg/ml), following the procedure described by Lin et al. (1989). SiON IOWs were treated with 1% dichlorodimethylsilane (DDS, Sigma), rinsed three times in deionized water, and then immersed in a solution of the acid-pretreated antibody 9-40 for 3 hr at room temperature.

Murine monoclonal anti-bovine serum albumin antibody (anti-BSA; available from Sigma) was labeled with Cy-5 as described for antibody 9-40. Bovine serum albumin (Sigma) was labeled with fluorescein isothiocyanate (FITC, Sigma). A 20-fold molar excess of FITC was added to a 1 mg/ml solution of BSA in CBB. This mixture was allowed to react for 1 hr at room temperature, and the conjugate was purified using a PD-10 column equilibrated in PBS. Labeling efficiency was approximately 2 FITC groups per BSA molecule. It should be noted that since the assays were performed with excitation at 632.8 nm, a wavelength which well exceeds the absorption band of FITC ($\lambda_{abs,max}$=492 nm), the FITC here serves solely as a hapten for 9-40, and not as a fluorescent tag.

Figure 5:
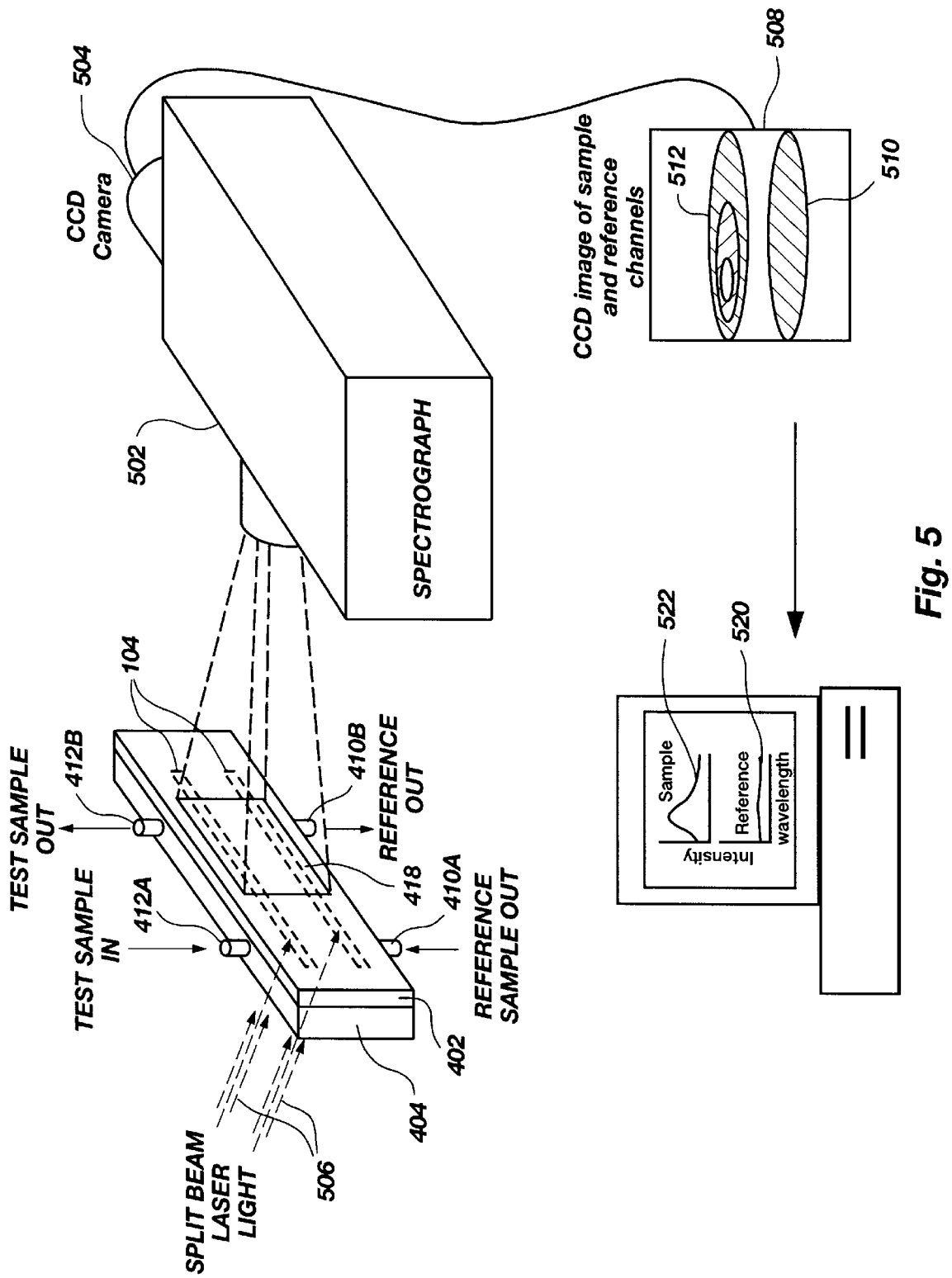
FIG. 5 is a schematic diagram of optical apparatus including the flow cell of FIGS. 4A and 4B, for performing binding assays therewith.

To perform the assays, IOWs coated as described in the preceding paragraphs were mounted in a flow cell like that of FIG. 4, and placed on a rotating goniometer (not shown) in the collection path of a spectrograph 502 associated with a CCD camera 504 (FIG. 5). The goniometer is optional, but useful in an experimental setup to ascertain the best coupling angle for coupling the laser beam into the waveguide. Once the best coupling angle has been determined and the apparatus standardized, a goniometer is not required to perform the assay. The input light was the red line (6 mW at 632.8 nm) of an HeNe laser (made by Melles Griot), split into dual beams 506, and simultaneously prism coupled into the two channels 104 of the composite waveguide. In this manner, a reference channel and a sample channel were excited.

For detection, the 1 mm wide guided modes in each channel were oriented perpendicular to the entrance slit of the spectrograph. Light emitted from a 1 mm long section of the two parallel streaks was imaged through the window 418 in the bottom plate 402 of the flow cell with a 50 mm f/5.6 camera lens onto the slit of spectrograph 502. The collected light emission was wavelength-dispersed using a single grating monochromator 502 (SPEX 1681c Minimate-2, f/3.9, 300 grooves/mm) centered at 700 nm, and directed onto a thermoelectrically-cooled CCD detector 504 (Photometrics Series 200), producing an image 508 containing reference region 510 and sample region 512. The reference and sample image regions 510, 512 were separately binned and vertically integrated and converted on a MACINTOSH IIx computer to reference spectrum 520 and sample spectrum 522, respectively, of intensity vs. wavelength.

Both assays followed the same general scheme: 1) a capture protein was immobilized to the surface of both the sample and reference channels; 2) aliquots of the hapten-carrier protein conjugate (with fluorescent tracer) were added to the sample channel; and 3) the same concentration of fluorescent tracer (without hapten) was added simultaneously to the reference channel.

Each measurement began by collecting the baseline spectra of PBS buffer in both the sample and reference channels. Starting with the most dilute analyte solution, 1 mL of the sample and reference solutions described in Table 1 were injected into the flow cell. The solutions were incubated with the waveguide surface for 2 min for assay 1 and 5 min for assay 2, followed by collection of 10 sec spectrograph images of both channels. This process was repeated several times until the most concentrated solution was assayed. All CCD images were collected without a wash step; i.e., with the fluorescent analyte filling the sample and reference channel volume. Reference and sample spectra derived from each CCD image of each measurement were integrated from 653 nm to 693 nm. Binding curves were constructed from these data by taking the ratio of the integrated intensity of the sample to that of the reference, and then plotting these ratios as a function of bulk analyte concentration. Such radiometric measurements compensated for two effects: nonspecific binding of the tracer, and parasitic excitation of bulk fluorescence.

Figure 6A:
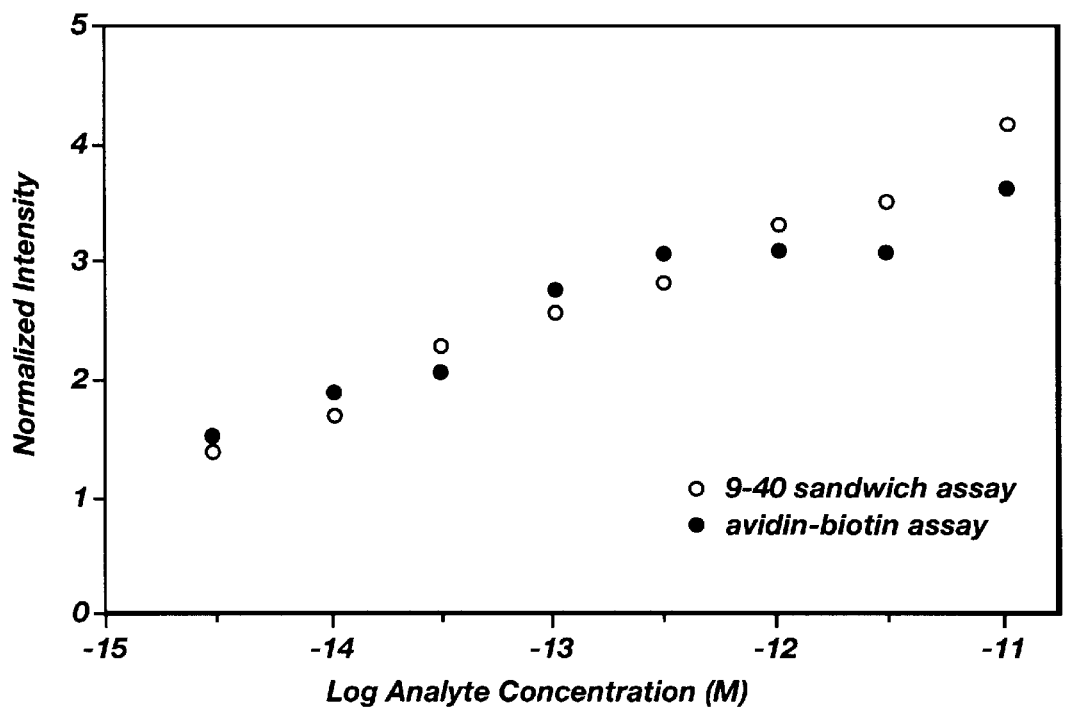
FIGS. 6A and 6B are charts of fluorescence measurements made with the apparatus of FIG. 4.
Figure 6B:
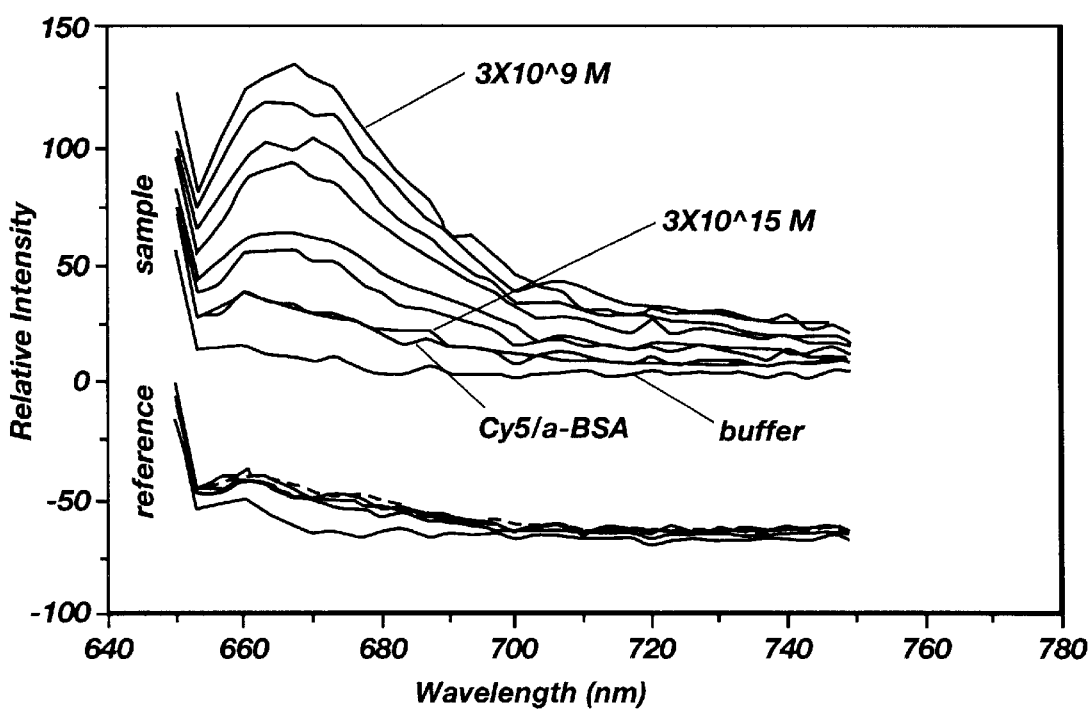

The results obtained with the two assay schemes are shown in FIGS. 6A–6B. The results indicate that analyte could be detected at concentrations as low as $3 \times 10^{-5}$M with a two-channel $Si_2O_3N$ thin film waveguide flow cell. These measurements are at least $3.3 \times 10^4$ times more sensitive than the thin film waveguide immunosensors reported by Sloper et al. or Zhou et al., op cit., and at least 33 times more sensitive than the thick film sensor of Herron et al. 1993, op cit.

The prism coupling scheme described in Example 4 is efficient, simple, and well suited for use in laboratory experiments. However, such a device is relatively expensive, and thus less than ideal for a disposable IOW module for use with a point-of-care optical unit. Further, the prism coupling scheme requires precise pressure on the prisms and precise alignment of the incident laser beam.

An alternate embodiment of a coupling scheme, which avoids these problems, is to provide a diffraction grating etched either into the surface of the waveguide opposite the substrate, or into the substrate adjacent the waveguide. The presently preferred embodiment is that of a substrate-etched grating. As seen in FIG. 2A, the substrate 102 has a grating 200 etched into the surface 102A which is in contact with the thin film 103. The binding molecules 106 are immobilized down-beam of the grating 200. Optionally, a second grating (not shown) may be etched into the substrate 102, down-beam of the immobilized binding molecules. Such a second grating is for purposes of optical characterization of the waveguide, and is not required for purposes of the fluorescence binding assay.

The depicted substrate-etched grating is advantageous in that the light can be conveniently in-coupled from the back side of the device, and without interference from macromolecules bound to the waveguide surface. Also, it is convenient and economical from a manufacturing perspective to etch the grating into the substrate prior to deposition and etching of the channel waveguides.

The efficiency of light incoupling by the etched grating will vary according to the spacing, the profile or blaze, and the aspect ratio of the grooves. These parameters should be optimized according to the wavelength of the input (excitation) light, the index of refraction of the superstrate, and the waveguide thickness, by techniques conventional in the art. In the present case, a grating period D4 of about 0.42 $\mu$m was computed for coupling of a normally incident 632.8 nm laser beam into the m=0 mode of the thin film SiON waveguide ($\theta = 83°$; see FIG. 2B).

Figure 3B:
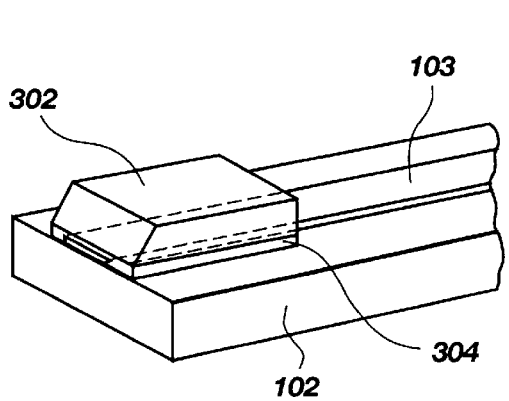
FIG. 3B is a perspective view of the embodiment of FIG. 3A.
Figure 3C:
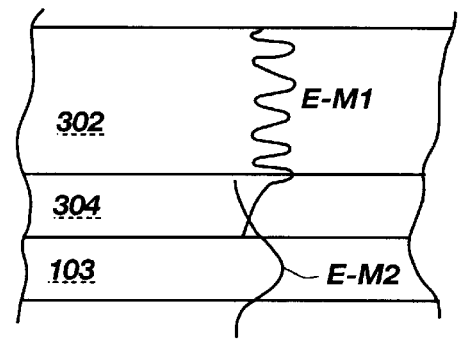
FIG. 3C is a schematic illustration of the overlap of the evanescent electromagnetic fields of the input waveguide and the thin film waveguide.

Still another coupling scheme uses the principle of evanescent penetration to evanescently couple light from a waveguide coupler into the composite waveguide across a precise spacing layer (FIGS. 3A, 3B and 3C). The waveguide coupler is contactingly mounted on the upper surface of the composite waveguide, adjacent the exposed surface of the thin film. Like the prism coupler, the waveguide coupler does not extend into the region to which the specific binding molecules are immobilized.

As seen in FIG. 3A, a waveguide coupler 300 comprises an input waveguide 302 which consists of a comparatively thick (1 mm or greater) layer of material of refractive index $n_3$, and a thin spacing layer 304 of refractive index $n_4$, where $n_4$ is less than both $n_3$ and $n_2$. The input waveguide has a receiving edge for receiving the input laser light, and a thickness D5 which is sufficient to allow easy end coupling of the input beam into the receiving edge. The spacing layer has a thickness D6 selected to maximize the evanescent coupling of waveguided light from the input waveguide into the thin film of the composite waveguide.

According to coupled mode theory, light propagating in one waveguide can be synchronously coupled into an adjacent waveguide if there is overlap between the evanescent regions of the two waveguides in the low index region separating them (FIG. 3C). The efficiency of coupling depends upon the spacing between the guides, the respective modal propagation constants, and the distance of the interaction. Since the coupling efficiency varies according to the cosine of the distance of interaction, in theory it will reach 100% at a certain length. Therefore, the synchronous evanescent coupling device should be quite efficient.

To achieve maximum coupling efficiency, the spacing layer thickness should be adjusted such that $$K_1 = (j+1)\pi/2, (j=0, 1, 2 \ldots)$$

where K is the coupling constant and depends on the refractive indices $n_1$, $n_2$, $n_3$, $n_4$, the wavelength lambda of the input light, and the respective thicknesses D2, D5 and D6 of the thin film waveguide, the input waveguide, and the spacing layer. With the thin film waveguide, it should be taken into account that generally, only one or a few of the lowest modes (preferably from j=0 to about j=10, and no more than j=20) are being propagated in the waveguide. Preferred waveguide couplers are configured to increase the proportion of laser light which is propagated in these lower modes.

For a silicon oxynitride composite waveguide, the spacing layer can be made of $SiO_2$. Desirably, the spacing layer 304 is deposited epitaxially, so that its thickness can be controlled very accurately at the time of deposition. The input waveguide 302 is attached on top of the spacing layer, after all epitaxial processing and etching steps have been finished in the fabrication of the composite waveguide. The input waveguide is made of a high refractive index material such as rutile, zirconia, or a high-index glass, and may be adhered to the spacing layer 302 by an index-matching cement of refractive index near $n_3$. This assembly would be comparatively inexpensive, and is thus attractive for a disposable, one-time use module.

Preferably, as shown in FIG. 3A, the laser light is focussed into the receiving edge of the input waveguide at an angle θ' which is a degree or two less than the critical angle for TIR at the interface between the input waveguide and the spacing layer. Such angled beam entry has been found to substantially increase the proportion of internally propagated light in the evanescent tail, and thus the evanescent intensity.

Figure 7:
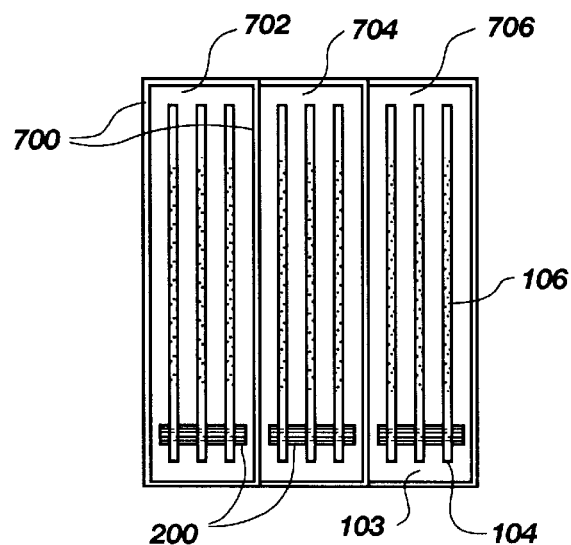
FIG. 7 is a top view of an alternate embodiment of a composite waveguide, having etched sample wells.

Still another embodiment is an IOW with integrally formed sample wells 702, 704, 706 (FIG. 7), each of which may contain multiple thin waveguide channels 104. In a preferred embodiment, walls 700 which enclose the wells are formed by layering a submicron cladding film of the substrate optical material on the composite waveguide, appropriately masking, and then etching the cladding back down to the SiON waveguide layer. These steps are performed prior to immobilization of the specific binding molecules. Sample wells thus constructed provide physically defined regions in which either different antibodies can be immobilized, or to which different solutions, e.g. background or control samples vs. test samples, can be added. The same technique could be used to form open-ended longitudinal flow channels instead of the box-shaped reservoirs illustrated. Also, instead of layering the reservoir wall material over the composite waveguide, the same technique could be used to form reservoir or flow channel walls on a separate top plate.

At present it is believed that two additional factors related to the chemistry of immobilization of specific binding molecules to the waveguide surface can affect the sensitivity achieved. These are 1) the relative amount of non-specific protein binding to the thin-film surface (including the walls of any sample wells); and 2) the analyte/tracer-binding capacity of the immobilized binding molecules.

In a highly preferred embodiment of the multi-channel IOW, the IOW surface is treated to minimize non-specific binding which otherwise can cause significant overlap of tracer signal between channels. The problem of such overlap worsens rapidly with increasing numbers of channels per IOW. Take as an example a six-channel waveguide divided into three adjacent-channel pairs in three corresponding separate wells, with anti-CK-MB immobilized to one member of each pair and anti-CK-MM immobilized to the other member. The IOW so constructed would permit simultaneous calibrated measurement of binding of 2 different analytes, CK-MB and CK-MM. If the level of non-specific binding is assumed to be about 5% of the specific binding level, the channel with anti-CK-MB covalently attached will be contaminated to about 5% with non-specifically adsorbed anti-CK-MM. Conversely, the channel with anti-CK-MM will be contaminated to about 5% with non-specifically adsorbed anti-CK-MB. Thus, with such a 2-analyte IOW there could be about 10% crosstalk between the channels, already an undesirable contribution to background level. For a 4-analyte IOW (twelve channels), however, the background contributed by such crosstalk would increase to about 30%, which would seriously impair detection sensitivity. Obviously, the problem worsens with increasing numbers of different analytes.

For this reason, it is highly desirable that the channels be coated with a coating that reduces non-specific binding to 1% or less of specific binding, prior to covalent immobilization of the specific binding molecule.

A method of enhancing the number of available analyte binding sites is to site-specifically immobilize the analyte binding molecules. For antigen-binding fragments such as F(ab')$_2$'s, this can be accomplished by providing a base coating having pendant maleimido groups. The F(ab')2 fragments are then reduced to yield Fab' fragments which contain a free thiol group at their C-terminal end, and this thiol group readily reacts to covalently couple the F(ab')$_2$ fragment to the maleimido group. Desirably, the coating with pendant maleimido groups also provides the inhibition of non-specific binding discussed in the preceding paragraph; this may for example be accomplished by a base coating comprising chains of polymerized hydrophilic residues adhered via a silica-affinic moiety to the waveguide surface, as disclosed by the copending U.S. patent application Ser. Nos. 08/064,608 and 08/263,522. Protocols for achieving both of these methods can be found in the noted copending applications, and in the literature in Herron et al., "Fluorescent immunosensors using planar waveguides", *SPIE* 1885:28–39, 1993. Preferably, at least 70% of the immobilized analyte binding molecules should be available for binding.

Introduction

Nucleic acid probes are gaining increasing acceptance in clinical diagnostics and may one day equal or surpass the importance of immunoassays. Because of their exquisite sensitivity, evanescent wave sensors have the potential of being able to detect DNA hybridization without prior amplification of the analyte. The strategy of this invention is to employ the nucleic acid analog of an immunological sandwich assay. Specifically, an oligonucleotide primer (capture oligonucleotide) complementary to the sequence of interest (analyte) is immobilized to the waveguide using either amine-reactive, thiol-reactive or the (strep)avidin-biotin coupling chemistry (see Herron, J. N., Caldwell, K. D., Christensen, D. A., Dyer, S., Hlady, V., Huang, P., Janatova, V., Wang, H.-K., and Wei, A.-P. "Fluorescent Immunosensors using Planar Waveguides," SPIE Vol. 1885 (Advances in Fluorescence Sensing Technology) 28–39 (1993).

Next, a fluorescent label such as Cy-5 is coupled to one end of a second oligonucleotide primer (tracer) which is complementary to another sequence on the analyte. To perform the assay, the analyte is first heated if it is double-stranded (to separate the two strands) and then mixed with the tracer oligonucleotide; this mixture is delivered to the sensor where the analyte hybridizes with the capture nucleotide and brings the tracer oligonucleotide into the evanescent field, where it (the tracer) fluoresces.

For detection of nucleic acids, the major technical barrier is the elimination of the amplification step (e.g., polymerase chain reaction), which is required in present-day assays to increase the amount of nucleic acid up to a measurable level. In theory, evanescent wave sensors possess the intrinsic sensitivity necessary to measure non-amplified DNA. However, there are many technical barriers to achieving this goal including development of (1) immobilization strategies which give very low levels of non-specific binding (perhaps 10- to 100-fold lower than present day technology); (2) effective reagent dispensing strategies that can deliver femtogram quantities of nucleic acid to the sensor surface without losses in a reasonable amount of time (5–10 min); and (3) effective strategies for denaturing double-stranded analytes into the single-stranded form required for hybridization assays.

Materials and Methods

Waveguides

Planar waveguides are employed for conducting fluorescent nucleic acid hybridization assays. Nucleic acid probes are immobilized as described below to either fused silica waveguides (1.0×1.0×0.1 cm, CO grade, ESCO) or injection molded polystyrene waveguides (1.0×1.0×0.05 cm, HCP Diagnostics, Salt Lake City).

Nucleic Acid Probes

The transcriptional promoter site of the T3 RNA polymerase is employed as a model oligonucleotide sequence in these studies. The T3 promoter is a 20-mer consisting of the following sequence: 5' AATTAACCCTCACTAAAGGG 3'. This oligonucleotide is synthesized and purified by a molecular biology service facility at the University of Utah. When used in DNA hybridization assays, it is immobilized to waveguides (using procedures described below) and used as the "capture" oligonucleotide. It is also used as the soluble inhibitor in competition assays. A second oligonucleotide sequence, complementary in sequence to the T3 promoter, is synthesized at the same service facility, fluorescently-labeled and used as the soluble "tracer" oligonucleotide in DNA hybridization assays. To this end, the oligonucleotide is synthesized with a terminal amino group on the 3' end and labeled with Cy-5 (Molecular Detection Systems, Pittsburgh), a red-emitting fluorescent dye.

Immobilization of Oligonucleotide Probes to Silica Waveguides

Oligonucleotide probes are coupled to silica waveguides using the avidin/biotin coupling chemistry. The general strategy is to immobilize avidin to the waveguides via electrostatic interactions (silica is negatively charged and avidin positively charged at neutral pH) and then complex biotinylated nucleotides to the immobilized avidin. Biotinylated oligonucleotides are prepared by coupling biotinamidocaproate N-hydroxysuccinimide ester (BCHS, Sigma) to a modified oligonucleotide that contained a 5' amino group. The BCHS derivative is used in order to provide a six carbon spacer between the 5' end of the oligonucleotide and the biotin moiety. The spacer is thought to provide the oligonucleotide with more conformational flexibility in hybridizing with other nucleotides. Specifically, a 20-fold molar excess of BCHS is added to a 0.1 mg/mL solution of oligonucleotide in 0.1M sodium carbonate/sodium bicarbonate buffer, pH 9 (CBB). This mixture is allowed to react for 2 hr at room temperature, and the product (biotinylated oligonucleotide) is purified by reverse phase FPLC chromatography (Pharmacia) using an acetylnitrile/$H_2O$ gradient. Avidin is immobilized to silica surfaces by physical adsorption. To this end, clean silica samples are immersed in an avidin solution [$3 \times 10^{-6}$M in phosphate buffered saline (PBS), pH 7.4] for 3 hr. at room temperature and then washed several times in the same buffer to remove unadsorbed avidin. Avidin-coated surfaces are then immersed in a $1.5 \times 10^{-7}$M solution of the biotinylated oligonucleotide in PBS for 1 hour at room temperature. Unbound nucleotide is removed by washing in PBS. In some cases, biotinylated poly(ethylene glycol) (biotin-PEG) is coupled to surfaces following the immobilization of biotinylated oligonucleotides. Biotin-PEG is prepared by reaction of N-hydroxysuccinimidobiotin (NHSB) with $NH_2$—PEG—$OCH_3$ (5000 MW, Sigma) for 2 hours in CBB, and purified by dialysis using Spectra/Por dialysis membranes (1000 MW cutoff). Silica surfaces (coated with avidin and oligonucleotides) are immersed in a solution of biotin-PEG ($5 \times 10^{-8}$M or $1 \times 10^{-7}$M) for 1 hour at room temperature. Unbound biotin-PEG is removed by washing in PBS.

Immobilization of Oligonucleotide Probes to Injection Molded Polystyrene Waveguides Similar procedures are employed for immobilizing oligonucleotides to polystyrene waveguides, except that strepavidin is used instead of avidin. Whereas avidin interacts strongly with silica substrates due to electrostatic interactions, our experience has shown that it does not adsorb nearly as well to polystyrene surfaces (which are uncharged and hydrophobic in nature). In contrast, strepavidin is the protein of choice for adsorption to polystyrene surfaces. Although functionally equivalent to avidin (i.e., it also contains four biotin binding sites), strepavidin possesses little charge at neutral pH and retains its biotin binding activity upon adsorption.

Total Internal Reflection Fluorescence Measurements

Total internal reflection fluorescence (TIRF) spectroscopy is an optical technique that is especially well-suited for measuring the concentration of fluorescent molecules attached to a solid surface such as a waveguide. Because water has a lower index of refraction than either silica or polystyrene, a beam of light traveling through a waveguide and striking its edge will either be refracted into the aqueous phase or reflected totally back into the waveguide, depending on the angle of incidence. In the latter case, the incident and reflected beams interfere to produce a standing wave in the waveguide. This wave has a finite electric field amplitude at the edge of the waveguide, but decays exponentially over a distance of 1000 to 2000 angstroms as one moves into the aqueous phase. This decaying electric field is referred to as the evanescent field.

Because the evanescent field is confined relatively close to the waveguide's surface, it can be used to detect nucleic acid hybridization reactions which occur at the surface. Waveguides are coated with oligonucleotides as described above and then mounted in the flowcell described in co-pending patent application Ser. No. 08/064,608. The fluorescence of the Cy-5 labeled tracer oligonucleotide is excited with either the 632.8 nm line of a He—Ne laser (Melles Griot) or the 633 nm line of a semiconductor laser (Power Technology, Inc.). The red line is formed into a sheet beam (with a cross-sectional area of ca. 0.2 cm×3 cm) and coupled simultaneously into the two channels (sample and reference) of the waveguide using a cylindrical coupling lens. The fluorescence emission of Cy-5 is collected using a 50 mm f/5.6 camera lens (Nikon) attached to a charge-coupled device (CCD) (either Photometrics Ltd Series 200 or Santa Barbara Instrument Group ST6). Fluorescence emission is discriminated from Rayleigh light scattering using either a single grating monochromator (SPEX 1681c Minimate-2, f/3.9, 300 grooves/mm) or a 670 nm bandpass interference filter (Omega).

Figure 8:
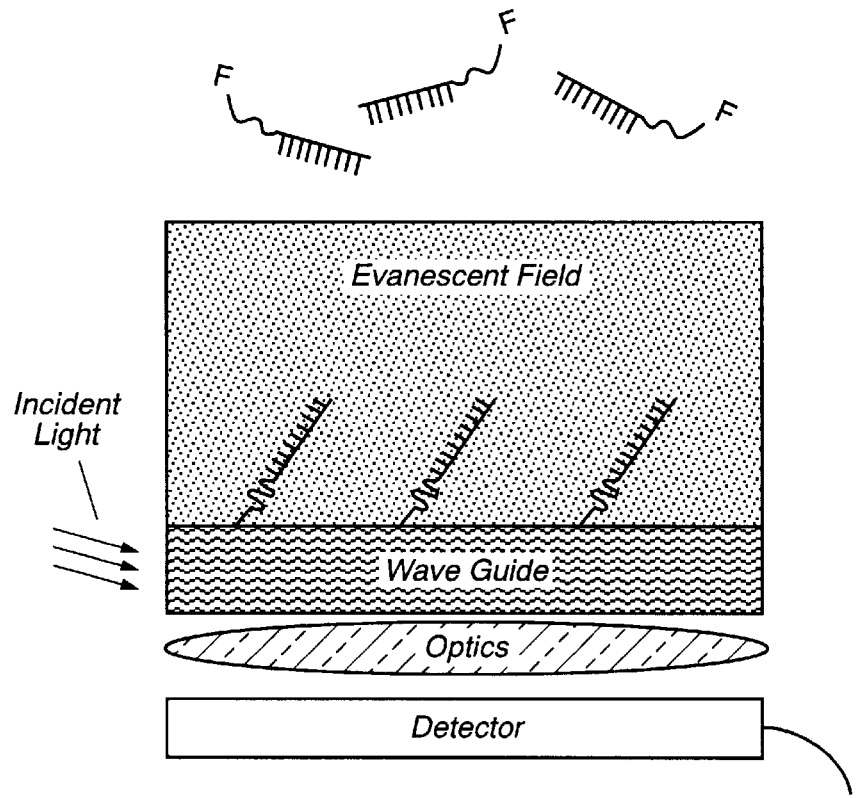
FIG. 8 is a schematic view of a sensor configured to detect a DNA macromolecule the sensor being illustrated in an initial configuration.
Figure 9:
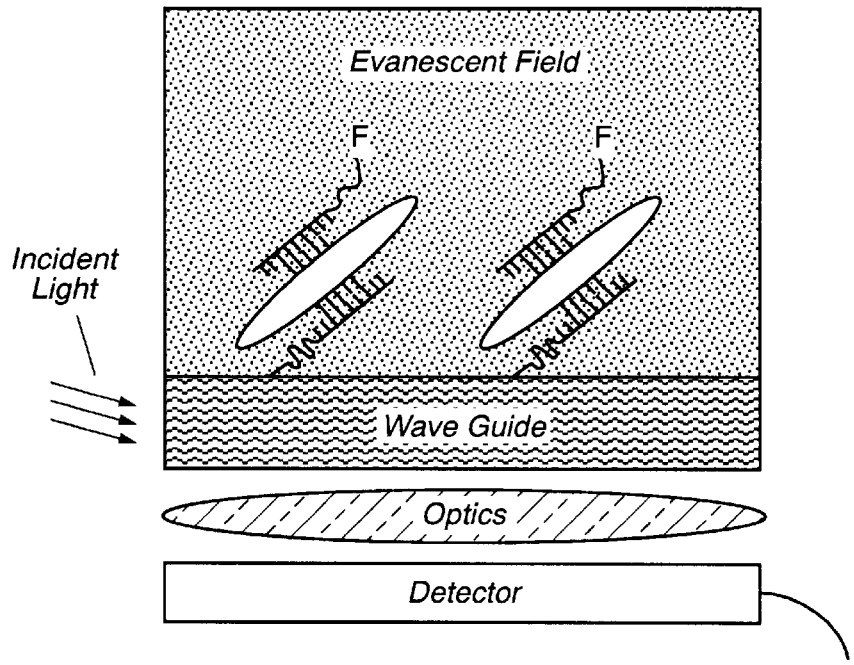
FIG. 9 is a schematic view of the sensor of FIG. 8 with an analyte shown being added.
Figure 10:
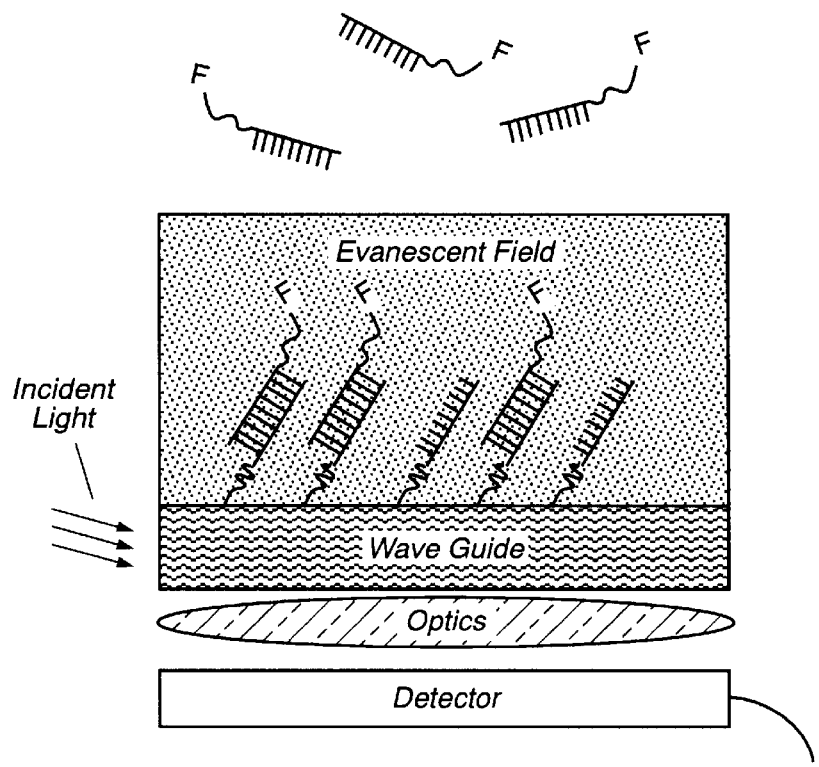
FIG. 10 is a schematic view of the configuration of Assay I.
Figure 11:
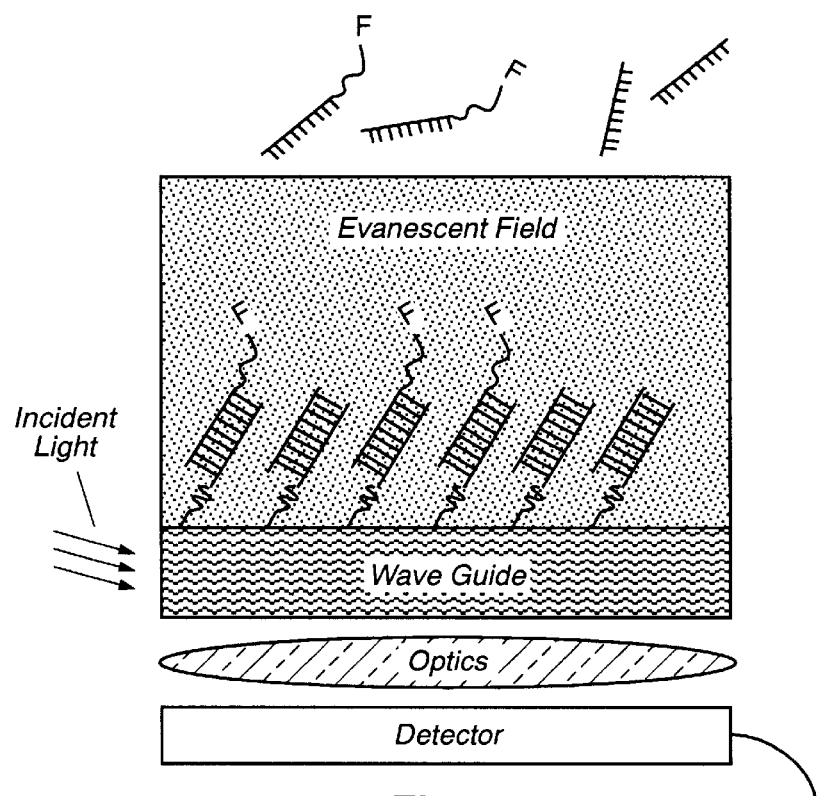
FIG. 11 is a schematic view of the configuration of Assay II.

In the general scheme, a "sandwich" assay is used to detect a DNA macromolecule (analyte) such as a plasmid or a large restriction fragment. Two oligonucleotide probes are employed for this purpose—a "capture" oligo that is immobilized to the waveguide and a soluble "tracer" oligo which is labeled with Cyanalyte and they should not hybridize to each other. The initial state of the sensor (before addition of analyte) is shown in FIG. 8. In this case, the tracer and capture oligonucleotides do not interact. Since there is very little fluorescent probe in the evanescent field, a low level of fluorescence is observed. Upon addition of analyte (FIG. 9), however, both capture and tracer oligos hybridize with the analyte to form a molecular sandwich on the waveguide. In this case the fluorescent probe is confined within the evanescent field and an increase in fluorescence is observed.

Assay Scheme

The use of planar waveguides and TIRF in detection of DNA hybridization is evaluated in two different assays. The first of these (Assay I) is a direct binding assay in which one strand of a DNA duplex is immobilized to the waveguide (referred to as the "immobilized strand") and the other strand (referred to as the "soluble strand") is labeled with a fluorescent dye. Formation of double-stranded DNA molecules on the waveguide is monitored as a function of the concentration of fluorescently-labeled soluble strand. The second assay (Assay II) is a competition assay based on the same reagents as described in Assay I. In this case, however, both labeled and unlabeled species of the soluble strand are present. Specifically, different concentrations of the unlabeled soluble strand are mixed with a fixed concentration of the labeled soluble strand and each mixture is allowed to react with the immobilized strand on a waveguide sensor. The formation of double-stranded DNA molecules is monitored using TIRF. Table II lists the reagents used in the two assays.

Assay I is a direct binding assay between two complementary oligonucleotides. The T3 RNA polymerase promoter site was chosen as a model system for our feasibility studies. The T3 promoter is a region spanning 20 bases with the following sequence: 5' AATTAACCCTCACTAAAGGG 3'. An oligonucleotide (T3 promoter) with this sequence was synthesized, biotinylated at the 5' end (via a spacer) and immobilized to waveguides (silica or polystyrene) coated with either avidin or stepavidin. A second nucleotide with a complementary sequence (anti Te) was also synthesized and labeled with Cy-5, a red-emitting fluorescent dye. Solutions with increasing tracer concentration were exposed to the waveguide and the fluorescence of bound tracer was plotted versus soluble tracer concentration. Assay II is a competitive binding assay in which unlabeled Anti T3 competes with Cy-5 labeled Anti T3 for binding to immobilized T3 promoter. In this case different concentrations of unlabeled Anti T3 were mixed with a fixed concentration of labeled Anti T3 (tracer). The fluorescence of bound tracer was measured for each mixture and plotted versus unlabeled Anti T3 concentration.

TABLE 2

Oligonucleotides used in TIRF-based DNA hybridization Assays†

| | immobilized oligonucleotide | sample channel | reference channel |
|---|---|---|---|
| Assay 1 | Biotinylated T3 Promoter | 1. Cy-5-labeled Anti T3 $(1 \times 10^{-13}$ to $10^{-8}M)$ | 1. Cy-5-labeled T3 Promoter $(1 \times 10^{-13}$ to $10^{-8}M)$ |
| Assay 2 | Biotinylated T3 Promoter | 1. Cy-5-labeled Anti T3 $(10^{-9}M)$ 2. Unlabeled Anti T3 $(1 \times 10^{13}$ to $10^{-9}M)$ | 1. Cy-5-labeled T3 $(10^{-9}M)$ |

†Abbreviations: Cy-5, an amino-reactive red-emitting fluorescent dye produced by Biological Detection Systems (Pittsburgh, PA); T3 Promoter, the transcriptional promoter site of T3 RNA polymerase which consists of the sequence 5' AATTAACCCTCACTAAAGGG 3'; Anti T3, oligonucleotide with a complementary sequence to the T3 promoter.

Figure 12:
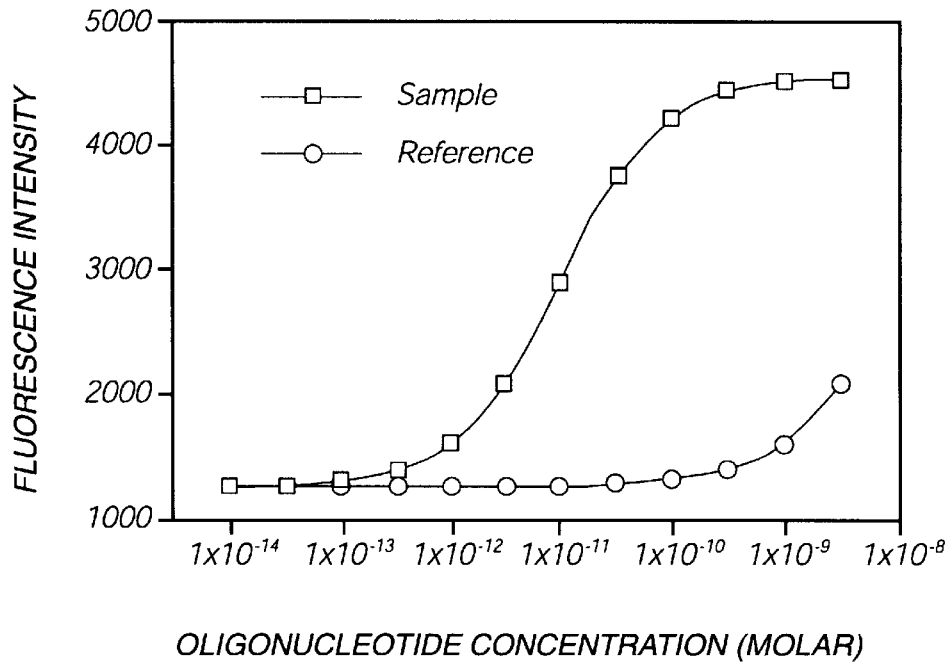
FIG. 12 is a graph of the oligonucleotide concentration versus fluorescence intensity for Assay I.
Figure 13:
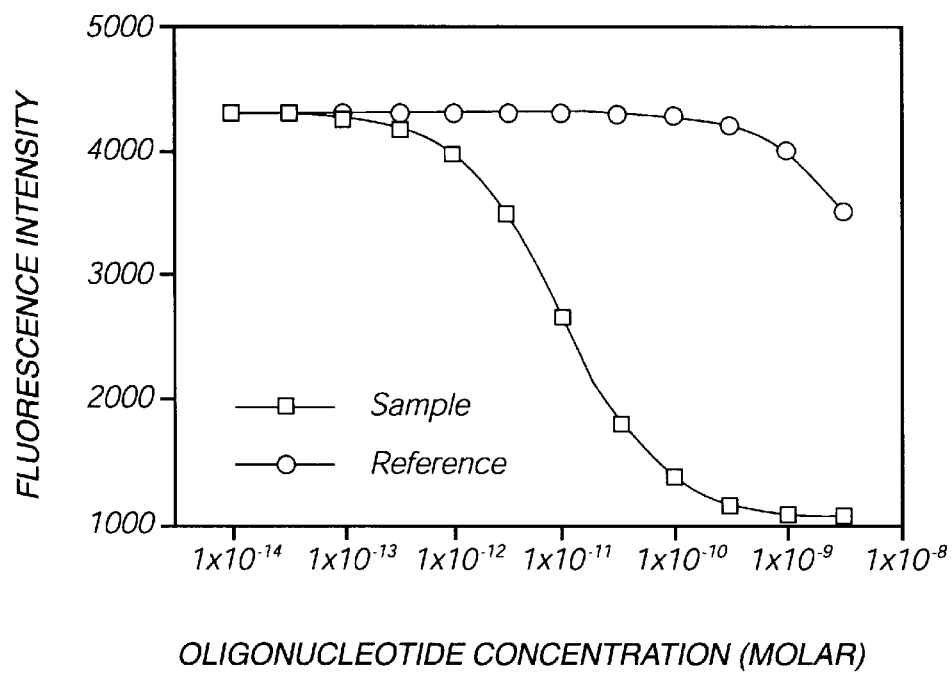
FIG. 13 is a graph of the oligonucleotide concentration versus fluorescence intensity for Assay II.
Figure 14:
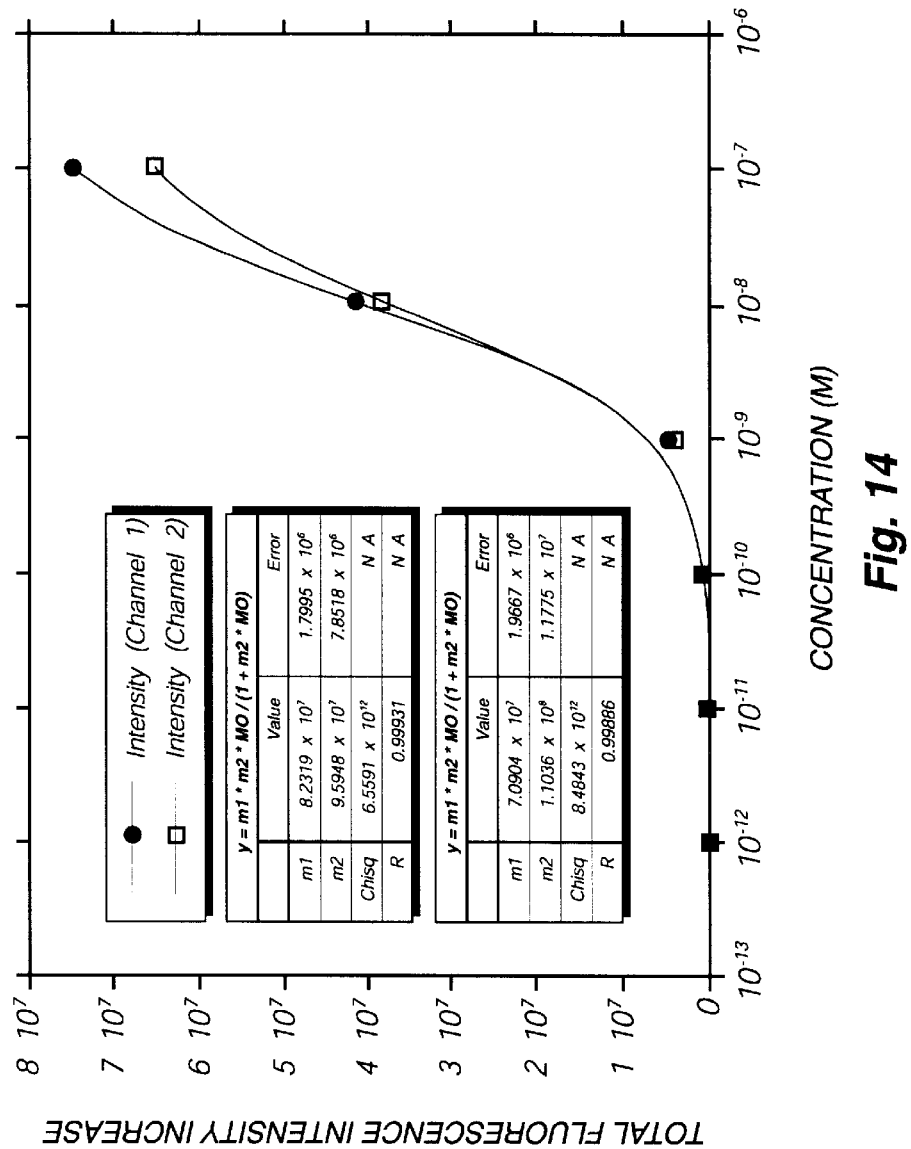
FIG. 14 is a graph of the equilibrium binding curves, showing concentration versus fluorescence intensity increase for Example 5.
Figure 15:
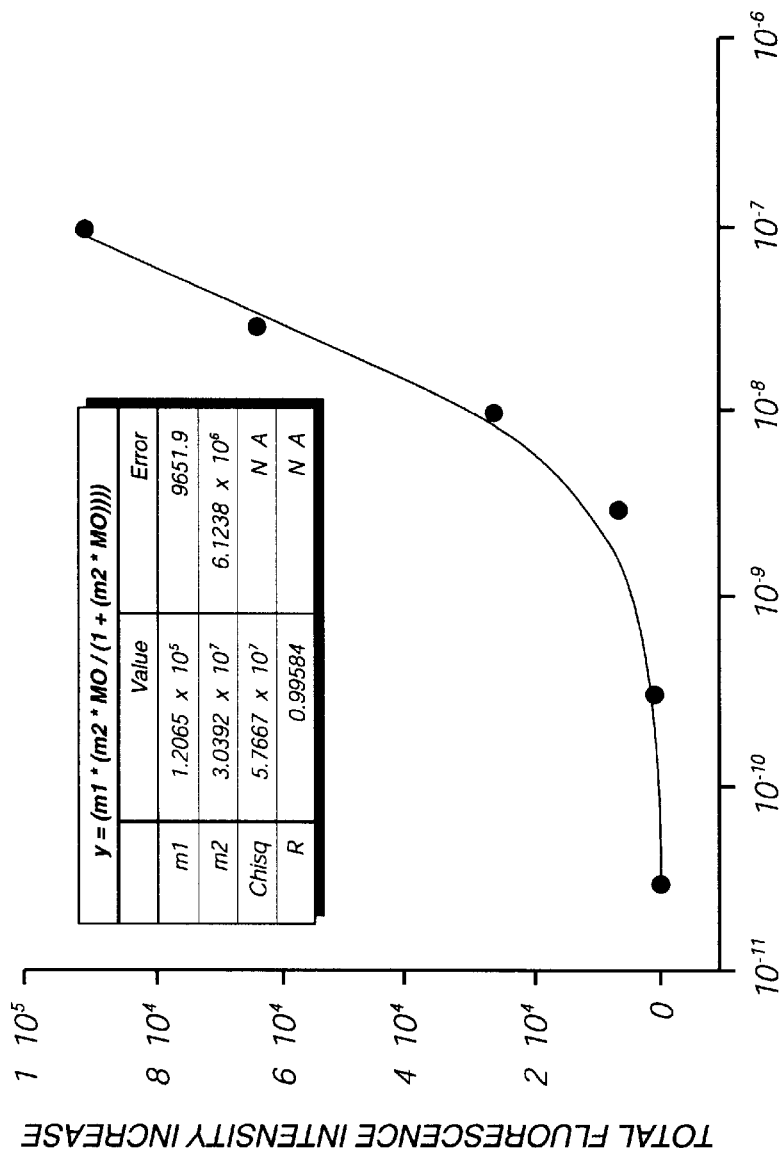
FIG. 15 is a graph of the equilibrium binding curves, showing CY5-labeled Oligo concentration versus fluorescence intensity increase for Example 6.
Figure 16:
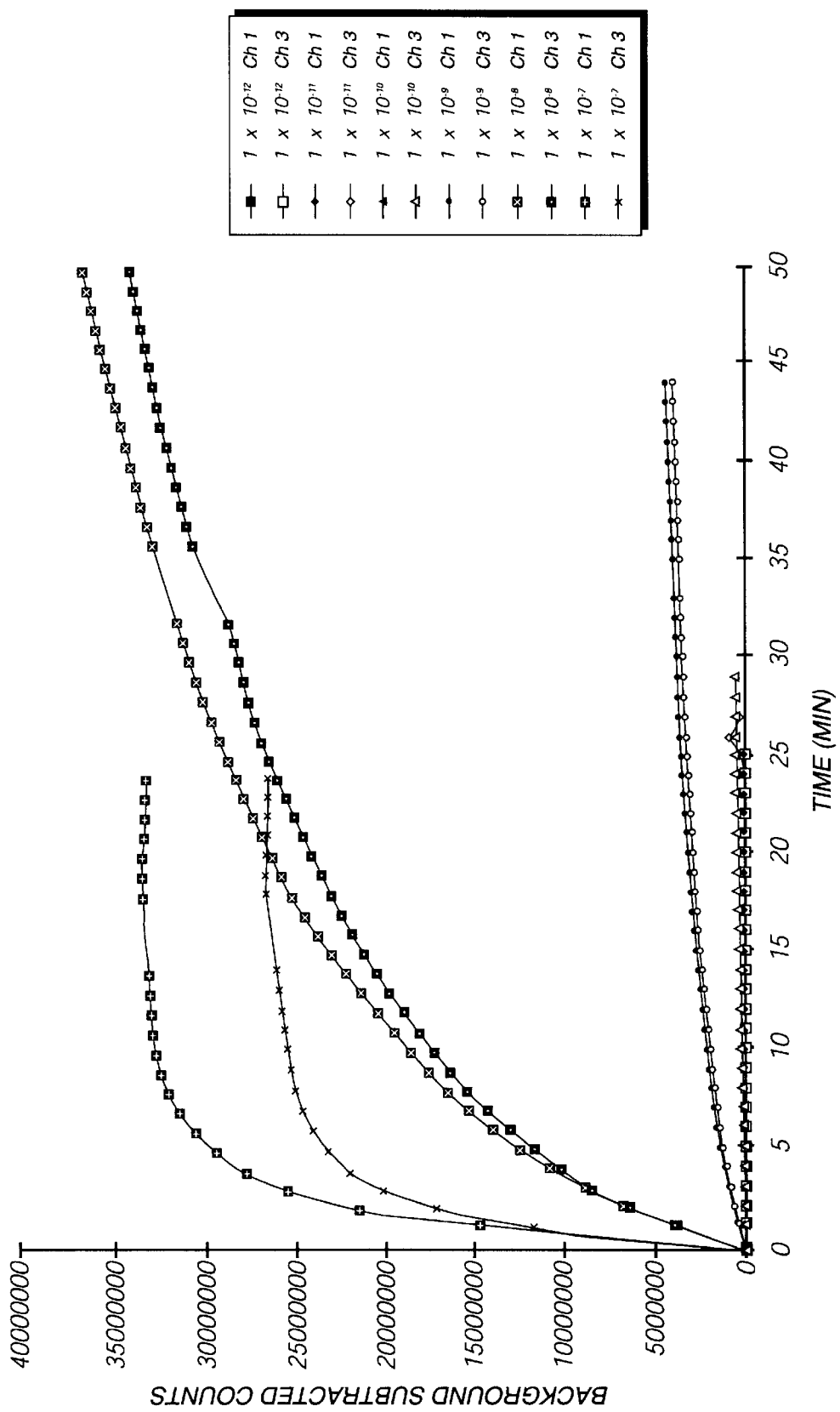
FIG. 16 is a graph illustrating the kinetics of increasing oligonucleotide Traus Concentration for Example 5.
Figure 16A:
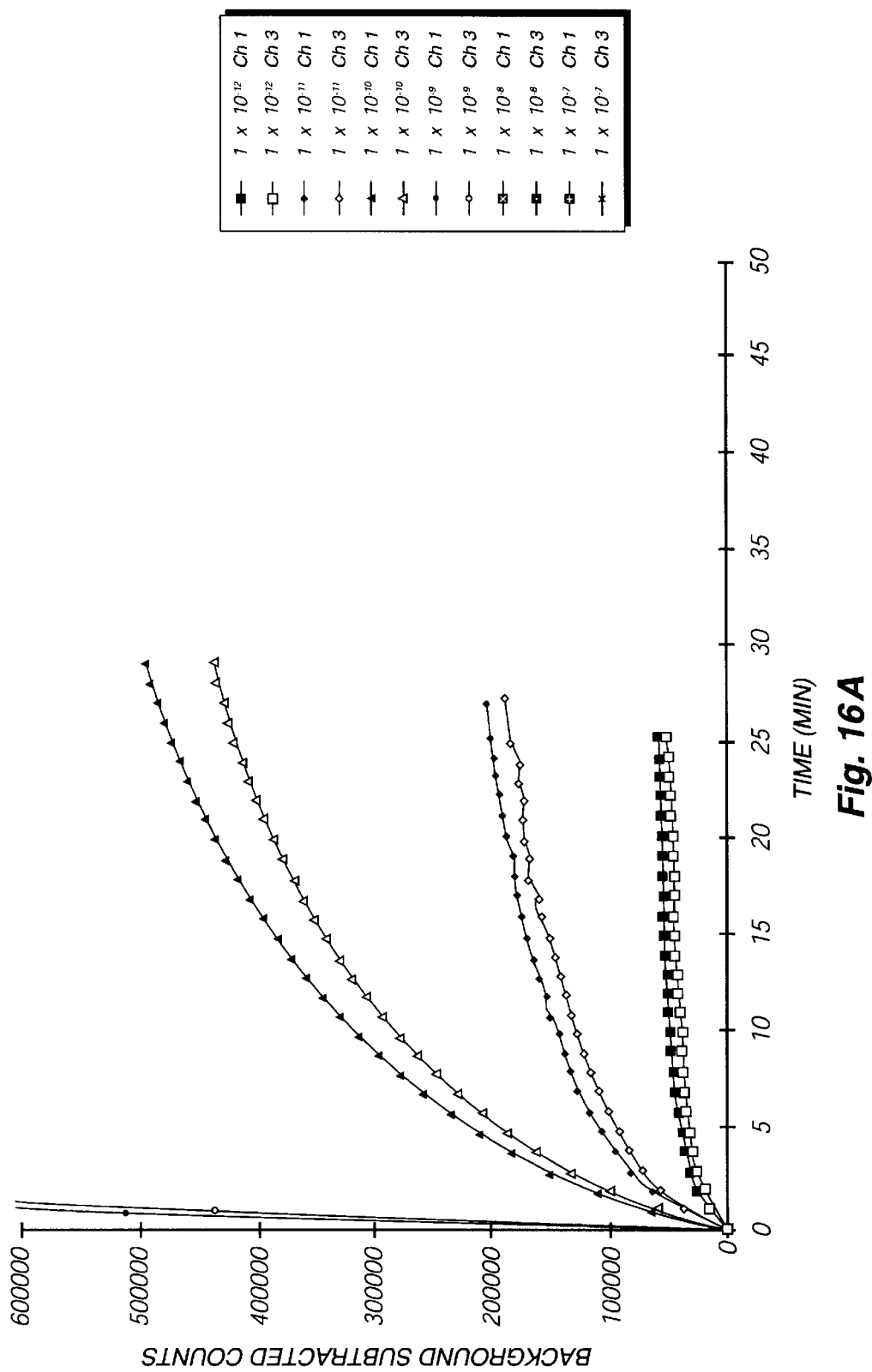
FIG. 16A is a sectional view of the graph of FIG. 16.
Figure 26:
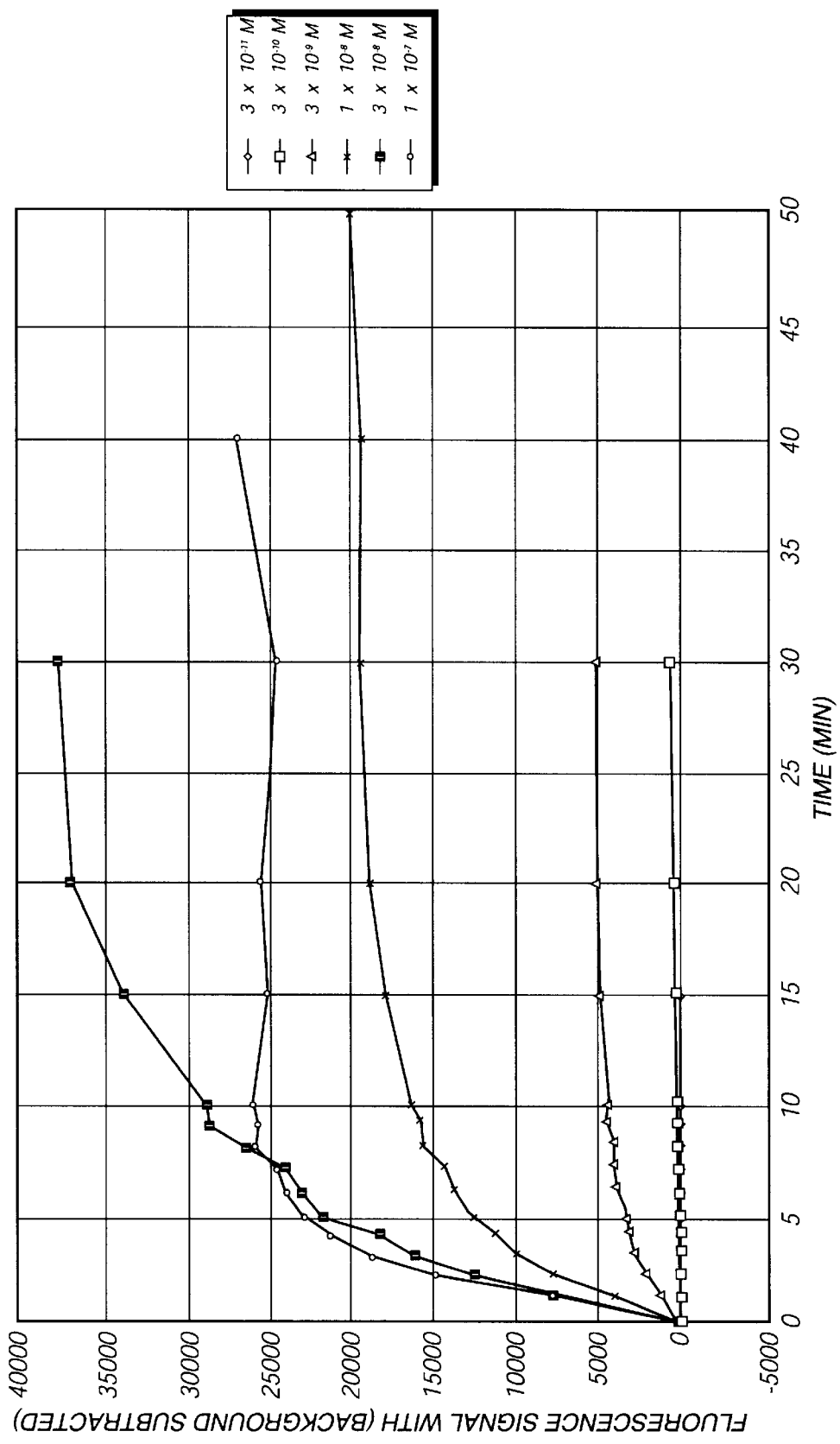
FIG. 26 is a graph illustrating the binding curves of the integrated Optic waveguide of Example 6.

Assays are performed using the two-channel flowcell described in co-pending patent application Ser. No. 08/064, 608. A "sample" solution containing the reagents described above is injected into one channel and a "reference" solution is injected into the other (see Table I for a description of sample and reference solutions employed in each assay). The reference solution is used to measure the degree of non-specific binding between the fluorescently-labeled oligonucleotide and the waveguide and also to correct for fluctuations in laser intensity that occurred during the course of an experiment. Each measurement begins by collecting the baseline fluorescence of PBS buffer in both the sample and reference channels. Starting with the most dilute analyte solution, 1 mL of the sample and reference solutions described in Table 2 are injected into the flowcell. The solutions are allowed to incubate with the waveguide surface for 5 minutes, followed by collection of 10 sec fluorescence images of both channels. This process is repeated several times until the most concentrated solution is assayed. All CCD images are collected without a wash step; i.e., with the fluorescent analyte filling the sample and reference channel volume. Binding curves are constructed from these data by taking the ratio of the intensity of the sample to that of the reference, and then plotting these ratios as a function of bulk analyte concentration. See FIGS. 12 and 13. Such radiometric measurements compensate for three effects—nonspecific binding of the tracer, excitation of bulk fluorescence by light scattered off the surface of the waveguide and fluctuations in laser intensity.

EXAMPLE 5

Polystyrene Waveguide Experiment

A polystyrene waveguide was coated with Avidin followed by incubation of the coated waveguide with a PBS buffer solution containing a biotinylated oligonucleotide (the 20 base anticompliment of the T3 promoter, sequence 5'-cc ttt agt gag ggt taa t-e'). Solutions of PBS buffer with varying concentrations of the CY5 labeled T3 promoter oligonucleotide were also prepared. The flow cell was assembled with the coated waveguide and the lowest concentration CY5 labled oligo solution was injected into the flow cell. CCD camera images were taken immediately following the injection and were continually taken at regular intervals to monitor binding kinetics. When image intensity ceased to increase significantly over time, a higher concentration solution of the CY5 labled T3 promoter was injected into the flow cell. The previous two steps were repeated with successively higher solution concentrations. The kinetic data were normalized by subtracting out the baseline at the beginning of each injection. See FIGS. 14 and 16–28. Each Kinetic curve levels off with time to the equilibrium value. The equilibrium values are successively added to generate a total signal increase for a given concentration. These total signal increase values are used in the equilibrium binding isotherm plots. The standard binding equilibrium equation was used to curve fit the equations. The curve fits of the data were very good and the total fluorescence increase was very high indicating that these data show a specific between the anticomplimentary pair of oligonucleotides.

EXAMPLE 6

Integrated Optic (IO) Waveguide Experiment

This procedure was similar to the polystyrene experiment with two exceptions. Only one flow cell channel was used in the IO experiment (hence there is only on equilibrium binding curve for the IO experiment). Also, light was coupled into the IO waveguide using a grating coupler rather than the lens coupler in the polystyrene waveguide. The results of Example 6 are shown in FIGS. 15 and 25–29.

It will be apparent that details of the composite waveguide can be varied considerably without departing from the concept and scope of the invention. The claims alone define the scope of the invention as conceived and as described herein.

What is claimed is:

1. A kit for performing specific binding assays with an optical unit including a light source positioned to direct light into an optical substrate and detector oriented to detect light from a region proximal to the optical substrate, which includes:

a biosensor comprising:

a step-gradient waveguide including a substrate formed of a first optical material of refractive index $n_1$ and having a surface disposed adjacent and in contact with a waveguide film formed of a second optical material having a refractive index $n_2$ which is greater than $n_1$, said substrate surface having a grating formed thereon, said grating constructed to facilitate coupling of light from an incident excitation beam into said waveguide film, said step-gradient waveguide being manufactured by a process of manufacture including the steps of:

providing a piece of the first optical material having a surface;

vapor depositing the second optical material on said first optical material surface to a depth of between about 0.1 $\mu$m and about 10 $\mu$m to produce said waveguide film;

coating at least one region of said waveguide layer film with a resist compound which resists an etchant to produce a coated region and an uncoated region; and etching said waveguide film with said etchant to remove said second optical material from said uncoated region; and at least one specific binding molecule immobilized to said waveguide film and constructed to bind with specificity an analyte.

2. The kit of claim 1, wherein said second optical material is selected from the group consisting of: silicon oxynitride of refractive index $n_2$, and deposited silicon dioxide; and said first optical material is selected from the group consisting of: deposited silicon dioxide, quartz or fused silica, silicon oxynitride of refractive index $n_1$, and magnesium fluoride.

3. The kit of claim 1, wherein said waveguide film is configured as a plurality of parallel longitudinal strips of said second optical material spaced from one another along said substrate surface and constituting a plurality of waveguide channels, and further having a plurality of different species of said at least one specific binding molecule immobilized to said waveguide film, with each of said waveguide channels having a different one of said species immobilized thereto.

4. The kit of claim 1, wherein said waveguide film is coated with a coating which provides a level of nonspecific protein binding which is less than about 10% of an amount of said specific binding of said analyte, said coating being selected from the group consisting of: polymethacryloyl polymer, polyethyleneglycol, and avidin.

5. The kit of claim 1, wherein said second optical material is selected from the group consisting of: silicon oxynitride of refractive index $n_2$, and silicon dioxide; and said first optical material is selected from the group consisting of: deposited silicon dioxide, quartz or fused silica, silicon oxynitride of refractive index $n_1$, and magnesium fluoride.

6. The kit of claim 1, in whose manufacture said step of coating at least one region with a resist compound comprises coating a plurality of parallel strips along said first optical material surface with said resist compound, thereby producing a plurality of waveguide channels, and wherein a plurality of different species of said at least one specific binding molecule is immobilized to said waveguide film, with each of said waveguide channels having a different one of said species immobilized thereto.

7. The kit of claim 6, whose manufacture further includes a step of etching a plurality of spaced grooves into said surface of said substrate prior to said step of depositing said waveguide layer second optical material, wherein said grooves are oriented substantially perpendicular to said waveguide channels, and spacing of said grooves is selected to serve as a grating facilitating efficient coupling of light from an incident excitation beam into said parallel strips.

8. The kit of claim 1, wherein said second optical material is silicon oxynitride having an elemental ratio of approximately $Si_2O_3N$.

9. A method of making a waveguide biosensor for performing specific binding assays with an optical unit including a light source positioned to direct light into an optical structure for propagation by total internal reflectance therein and detection means oriented to detect light from a region proximal to the optical structure, said optical structure constructed by the steps of:

providing a substrate comprising a first optical material of refractive index $n_1$ and having two parallel planar surfaces separated by a thickness and a surrounding edge;

depositing a waveguide layer of a second optical material having a refractive index $n_2$ on one of said surfaces, said waveguide layer having a thickness which is between about 0.1 $\mu$m and about 10 $\mu$m and $n_2$ being greater than $n_1$;

coating at least one region of said waveguide layer with a resist compound which resists an etchant to produce a coated region and an uncoated region;

etching said waveguide layer with said etchant to remove said second optical material from the uncoated region;

removing the resist compound from the etched waveguide later to expose the coated region; and immobilizing a plurality of capture molecules to said exposed coated region, said capture molecules being constructed to bind with specificity a selected analyte molecule.

10. The method of claim 9, further including a step of coating said exposed coated region with a coating which provides a level of nonspecific protein binding which is less than about 10% of a amount of said specific binding of said analyte, said coating being selected from the group consisting of: polymethacryloyl polymer, polyethyleneglycol, and avidin; and wherein in said step of immobilizing capture molecules, said capture molecules are bound to said coating.

11. The method of claim 10, wherein said second optical material is selected from the group consisting of: silicon oxynitride of refractive index $n_2$, and deposited silicon dioxide; and said first optical material is selected from the group consisting of: deposited silicon dioxide, quartz or fused silica, silicon oxynitride of refractive index $n_1$, and magnesium fluoride.

12. A kit for performing specific binding assays with an optical unit including a light source positioned to direct light into an optical substrate and detection means oriented to detect light from a region proximal to the waveguide, which includes:

a biosensor comprising:
      a step gradient waveguide including:
         a substrate formed of a first optical material of refractive index $n_1$ and having a surface disposed adjacent and in contact with a waveguide film formed of a second optical material having a refractive index $n_2$ which is greater than $n_1$; and
      a waveguide coupler contactingly disposed on said waveguide film, said waveguide coupler comprising:
         an input waveguide formed of an optical material having a refractive index $n_3$, and having a thickness which is between about 0.5 mm and about 5 mm; and
         a spacing layer formed of an optical material having a refractive index $n_4$, wherein $n_4<n_3$ and $n_4<n_2$, and having a thickness selected to optimize evanescent coupling of light from said input waveguide into said waveguide film and
   at least one specific binding molecule immobilized to said waveguide film and constructed to bind with specificity an analyte.

* * * * *

UNITED STATES PATENT AND TRADEMARK OFFICE
CERTIFICATE OF CORRECTION

PATENT NO : 5,832,165
DATED : November 3, 1998
INVENTOR(S) : Reichert et al.

It is certified that error appears in the above-identified patent and that said Letters Patent is hereby corrected as shown below:

Column 3, line 56, change "The (IOW)" to --The waveguide (IOW)--;

Column 11, line 36, change "$3 \times 10^{-5}M$" to --$3 \times 10^{-15}M$--;

Column 14, line 14, insert commas after "may" and "example";

Column 17, line 35, change "stepavidin" to --strepavidin--;

Column 17, line 58 change "labeled T3" to --labeled Anti T3--;

Claim 1, Column 19, line 33, after "waveguide" delete --layer--;

Claim 7, Column 20, line 19, delete "waveguide layer";

Claim 9, Column 20, line 51, change "later" to --layer--; and

Claim 12, Column 21, line 9, change "waveguide" to --optical substrate--.

Signed and Sealed this

Sixth Day of June, 2000

Q. TODD DICKINSON

Attest:

Attesting Officer

Director of Patents and Trademarks